(12) United States Patent
Almsick et al.

(10) Patent No.: US 6,703,348 B2
(45) Date of Patent: Mar. 9, 2004

(54) HETEROCYCLYL-SUBSTITUTED BENZOYLCYCLOHEXANDIONES, THEIR PREPARATION, AND THEIR USE AS HERBICIDES

(75) Inventors: Andreas van Almsick, Karben (DE); Lothar Willms, Hofheim (DE); Thomas Auler, Bad Soden (DE); Hermann Bieringer, Eppstein (DE); Felix Thürwächter, Dreieich (DE)

(73) Assignee: Aventis CropScience GmbH, Frankfurt (DE)

( * ) Notice: Subject to any disclaimer, the term of this patent is extended or adjusted under 35 U.S.C. 154(b) by 35 days.

(21) Appl. No.: 09/943,040

(22) Filed: Aug. 30, 2001

(65) Prior Publication Data

US 2002/0173424 A1 Nov. 21, 2002

(30) Foreign Application Priority Data

Sep. 1, 2000 (DE) .......................... 100 43 075

(51) Int. Cl.⁷ ........................ A01N 43/72; C07D 498/04
(52) U.S. Cl. ....................... 504/271; 548/242
(58) Field of Search ............... 504/271; 548/242

(56) References Cited

U.S. PATENT DOCUMENTS 6,004,903 A    12/1999    von Deyn et al. ........ 504/239

FOREIGN PATENT DOCUMENTS

| EP | 0 894 792 | * | 2/1999 |
|----|-----------|---|--------|
| WO | WO 96/26200 |   | 8/1996 |
| WO | 96/262000 | * | 8/1996 |
| WO | 0005221   |   | 2/2000 |
| WO | 00/05221  | * | 2/2000 |
| WO | 00/21924  | * | 4/2000 |
| WO | 00/39094  | * | 7/2000 |
| WO | 01/40200  | * | 6/2001 |
| WO | 01/07422  | * | 2/2002 |

* cited by examiner

Primary Examiner—John M. Ford
(74) Attorney, Agent, or Firm—Frommer Lawrence & Haug LLP

(57) ABSTRACT

There are described benzoylcyclohexanediones of the formula I, their preparation, and their use as herbicides and plant growth regulators.

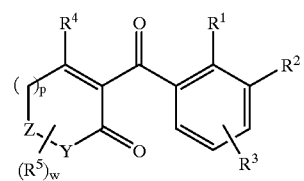

(I)

In this formula (I), $R^1$, $R^2$, $R^3$, $R^4$, $R^5$, $R^6$, $R^7$, $R^a$, $R^b$ and $R^c$ are various radicals, and Y and Z are a monoatomic bridge element.

12 Claims, No Drawings

HETEROCYCLYL-SUBSTITUTED BENZOYLCYCLOHEXANDIONES, THEIR PREPARATION, AND THEIR USE AS HERBICIDES

The invention relates to the technical field of the herbicides, in particular that of the herbicides for the selective control of broad-leaved weeds and grass weeds in crops of useful plants.

It is already known from various publications that certain benzoylcyclohexanediones, including those which are substituted in the 3-position of the phenyl ring, for example by a heterocyclic radical, have herbicidal properties. Such benzoylcyclohexane diones are particularly suitable for controlling harmful plants in maize. WO 96/26200 describes benzoylcyclohexanediones which have a 5- or 6-membered heterocycle attached in the 3-position of the phenyl ring. This heterocycle can be saturated or unsaturated and substituted or unsubstituted. Moreover, this heterocycle may form a bicyclic system together with a fused second ring.

However, the application of the benzoylcyclohexanediones known from these publications frequently entails disadvantages in practice. Thus, the herbicidal activity of the known compound is not always sufficient, or else, while the herbicidal activity is sufficient, undesirable damage is observed on the crop plants. In particular, the harmful Setaria species, which are considered to be a particular problem in the United States, which constitute the world's largest market for maize, are only controlled insufficiently by the known benzoylcyclohexanediones. The object of the present invention was therefore to provide herbicidally active compounds with herbicidal properties which are improved over those of the prior-art compounds, in particular for use in maize crops.

It has now been found that benzoylcyclohexanediones which have certain radicals selected from the group of the oligocyclic radicals attached in the 3-position of the phenyl ring are particularly well suited as herbicides. A subject of the present invention is therefore compounds of the formula (I) or their salts

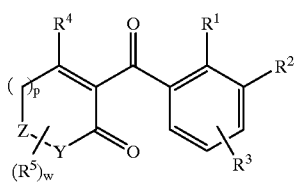

(I)

in which
R$^1$ is halogen, $(C_1–C_4)$-alkyl, halogen-$(C_1–C_4)$-alkyl, $(C_1–C_4)$-alkylsulfenyl, $(C_1–C_4)$-alkylsulfinyl, $(C_1–C_4)$-alkylsulfonyl or nitro;
R$^2$ is a radical AB(C)$_q$(D)$_o$ which is linked to the benzoyl moiety via A;
AB(C)$_q$(D)$_o$ is a bi-, tri- or tetracyclic radical, where
  a) A, B, C and D are in each case a 3- to 8-membered, saturated, partially saturated, unsaturated or aromatic ring containing 1 to 4 hetero atoms selected from the group consisting of oxygen, nitrogen and sulfur,
  b) the rings A, B, C and D are in each case substituted by v substituents selected from the group consisting of R$^6$, halogen, cyano, nitro, hydroxyl, oxo, $(C_1–C_4)$-alkyl, halogen-$(C_1–C_4)$-alkyl, $(C_1–C_4)$-alkoxy, halogen-$(C_1–C_4)$-alkoxy and di-$(C_1–C_4)$-alkylamino,
  c) two rings A, B, C and D are linked to each other via two joint atoms,
  d) B is not the benzo group when A contains at least one hetero atom;
R$^3$ is halogen, halogen-$(C_1–C_4)$-alkyl, $(C_1–C_4)$-alkylsulfinyl, $(C_1–C_4)$-alkylsulfinyl, $(C_1–C_4)$-alkylsulfonyl or nitro;
R$^4$ is OR$^7$, $(C_1–C_4)$-alkylthio, halogen-$(C_1–C_4)$-alkylthio, $(C_1–C_4)$-alkenylthio, halogen-$(C_2–C_4)$-alkenylthio, $(C_2–C_4)$-alkynylthio, halogen-$(C_2–C_4)$-alkynylthio, $(C_2–C_4)$-alkylsulfinyl, halogen-$(C_2–C_4)$-alkylsulfinyl, $(C_2–C_4)$-alkenylsulfinyl, halogen-$(C_2–C_4)$-alkenylsulfinyl, $(C_2–C_4)$-alkynylsulfinyl, halogen-$(C_2–C_4)$-alkynylsulfinyl, $(C_1–C_4)$-alkylsulfonyl, halogen-$(C_1–C_4)$-alkylsulfonyl, $(C_2–C_4)$-alkenylsulfonyl, halogen-$(C_2–C_4)$-alkenylsulfonyl, $(C_2–C_4)$-alkynylsulfonyl, halogen-$(C_2–C_4)$-alkynylsulfonyl, cyano, cyanato, thiocyanato, halogen, or is phenylthio which is substituted by v radicals selected from the group consisting of halogen, $(C_1–C_4)$-alkyl, $(C_1–C_4)$-alkoxy, halogen-$(C_1–C_4)$-alkyl, halogen-$(C_1–C_4)$-alkoxy, cyano and nitro;
R$^5$ is tetrahydropyranyl-3, tetrahydropyranyl-4, tetrahydrothiopyranyl-3, $(C_1–C_4)$-alkyl, $(C_3–C_8)$-cycloalkyl, $(C_1–C_4)$-alkoxy, $(C_1–C_4)$-alkoxy-$(C_1–C_4)$-alkyl, $(C_1–C_4)$-alkylcarbonyl, $(C_1–C_4)$-alkoxycarbonyl, $(C_1–C_4)$-alkylthio, phenyl, the eight last-mentioned groups being substituted by v radicals selected from the group consisting of halogen, $(C_1–C_4)$-alkylthio and $(C_1–C_4)$-alkoxy or two radicals R$^5$ bonded to a joint carbon atom form a chain selected from the group consisting of OCH$_2$CH$_2$O, OCH$_2$CH$_2$CH$_2$O, SCH$_2$CH$_2$S and SCH$_2$CH$_2$CH$_2$S, these being substituted by w methyl groups, or two radicals R$^5$ bonded to directly adjacent carbon atoms form a bond or, together with the carbon atoms to which they are attached, form a 3- to 6-membered ring substituted by w radicals selected from the group consisting of halogen, $(C_1–C_4)$-alkyl, $(C_1–C_4)$-alkylthio and $(C_1–C_4)$-alkoxy;
R$^6$ is straight-chain or branched [C(R$^8$)$_2$]$_m$-(G)$_p$-[C(R$^8$)$_2$]$_m$-R$^9$;
R$^7$ is hydrogen, $(C_1–C_4)$-alkyl, halogen-$(C_1–C_4)$-alkyl, $(C_1–C_4)$-alkoxy-$(C_1–C_4)$-alkyl, formyl, $(C_1–C_4)$-alkylcarbonyl, $(C_1–C_4)$-alkoxycarbonyl, $(C_1–C_4)$-alkylaminocarbonyl, di-$(C_1–C_4)$-alkylaminocarbonyl, $(C_1–C_4)$-alkylsulfonyl, halogen-$(C_1–C_4)$-alkylsulfonyl, benzoyl or phenylsulfonyl, the two last-mentioned groups being substituted by v radicals selected from the group consisting of $(C_1–C_4)$-alkyl, halogen-$(C_1–C_4)$-alkyl, $(C_1–C_4)$-alkoxy, halogen-$(C_1–C_4)$-alkoxy, halogen, cyano and nitro;
R$^8$ is hydrogen, $(C_1–C_4)$-alkyl or halogen;
R$^9$ is OR$^{13}$, SR$^{13}$, SOR$^{13}$, SO$_2$R$^{13}$, CO$_2$R$^{14}$, CONR$^{14}$R$^{15}$, N(R$^{14}$)COR$^{15}$, N(R$^{14}$)SO$_2$R$^{15}$, P(O)R$^{14}$R$^{15}$, halogen, cyano, nitro, $(C_3–C_8)$-cycloalkyl, $(C_3–C_8)$-cycloalkyl, aryl, 5- or 6-membered heterocyclyl or heteroaryl with in each case one to four hetero atoms selected from the group consisting of oxygen, sulfur and nitrogen, it being possible for these five abovementioned radicals to be substituted by v substituents selected from the group consisting of halogen, cyano, formyl, nitro, $(C_1–C_4)$-alkyl, halogen-$(C_1–C_4)$-alkyl, $(C_1–C_4)$-alkoxy, halogen-$(C_1–C_4)$-alkoxy, $(C_1–C_4)$-alkylthio, halogen-$(C_1–C_4)$-alkylthio and R$^{10}$, or is a radical of the formula Va to Vt:

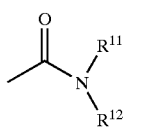 (Va)

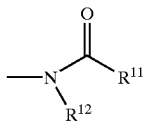 (Vb)

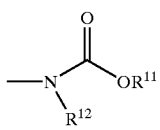 (Vc)

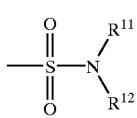 (Vd)

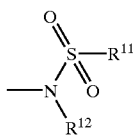 (Ve)

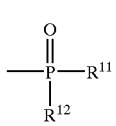 (Vf)

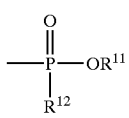 (Vg)

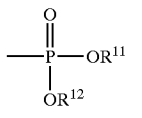 (Vh)

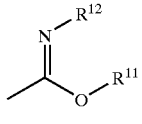 (Vi)

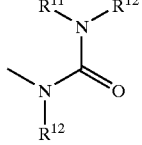 (Vj)

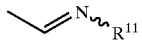 (Vk)

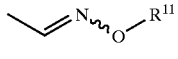 (Vl)

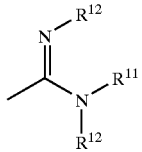 (Vm)

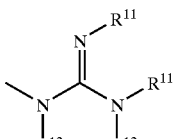 (Vn)

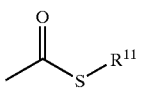 (Vo)

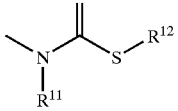 (Vp)

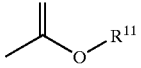 (Vq)

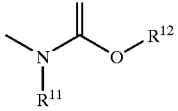 (Vr)

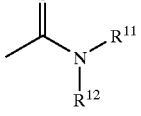 (Vs)

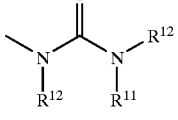 (Vt)

$R^{10}$ is [$(C_1-C_4)$-alkylene-O—$(C_1-C_4)$-alkylene]$_n$-O—$(C_1-C_4)$-alkyl, or is $(C_1-C_4)$-alkyl, $(C_2-C_4)$-alkenyl or $(C_2-C_4)$-alkynyl, each of which is substituted by v halogen atoms;

$R^{11}$ is hydrogen, $(C_1-C_4)$-alkyl, $(C_1-C_4)$-alkoxy, $(C_2-C_4)$-alkenyl, $(C_2-C_4)$-alkynyl, $(C_3-C_8)$-cycloalkyl, aryl, aryl-$(C_1-C_6)$-alkyl, heteroaryl, heterocyclyl, halogen-$(C_1-C_4)$-alkyl;

$R^{12}$ is hydrogen, $(C_1-C_4)$-alkyl, $(C_2-C_4)$-alkenyl, $(C_2-C_4)$-alkynyl, $(C_3-C_9)$-cycloalkyl, aryl, aryl-$(C_1-C_6)$-alkyl, heteroaryl, heterocyclyl, halogen-$(C_1-C_4)$-alkyl, or, if $R^{11}$ and $R^{12}$ are bonded to one atom or to two directly adjacent atoms, they form together with the atoms binding them a saturated, partially or fully unsaturated five- to six-membered ring which contains p hetero atoms selected from the group consisting of oxygen, nitrogen and sulfur;

$R^{13}$ is $R^7$, $(C_2-C_6)$-alkenyl, $(C_2-C_6)$-alkynyl, $(C_3-C_8)$-cycloalkyl, $(C_3-C_8)$-cycloalkenyl or $(C_3-C_8)$-cycloalkyl-$(C_1-C_6)$-alkyl;

$R^{14}$ and $R^{15}$ independently of one another are hydrogen, $(C_1-C_6)$-alkyl, $(C_1-C_6)$-alkoxy, $(C_2-C_6)$-alkenyl, $(C_2-C_6)$-alkenyloxy, $(C_2-C_6)$-alkynyl, halogen-$(C_1-C_6)$-alkyl, $(C_3-C_8)$-cycloalkyl, cyano-$(C_1-C_6)$-alkyl, halogen-$(C_2-C_6)$-alkenyl, halogen-$(C_2-C_6)$-alkynyl, substituted or unsubstituted aryl or substituted or unsubstituted aryl-$(C_1-C_6)$-alkyl;

G is oxygen or sulfur;

Y is a divalent unit selected from the group consisting of O, S, N—H, N—($C_1$–$C_4$)-alkyl, $CHR^5$ and $C(R^5)_2$;

Z is a divalent unit selected from the group consisting of O, S, SO, $SO_2$, N—H, N—($C_1$–$C_4$)-alkyl, $CHR^5$ and $C(R^5)_2$;

m and n independently of one another are 0, 1 or 2;

o, p and q independently of one another are 0 or 1;

v is 1, 1, 2 or 3;

w is 0, 1, 2, 3 or 4.

A large number of compounds of the formula (I) according to the invention can exist in different tautomeric structures, depending on external conditions such as solvent and pH. Depending on the nature of the substituents, the compounds of the formula (I) contain an acidic proton which can be removed by reaction with a base. Examples of suitable bases are hydrides, hydroxides and carbonates of lithium, sodium, potassium, magnesium and calcium, or else ammonia and organic amines such as triethylamine and pyridine. Such salts are also subject of the invention.

In all the formulae mentioned hereinbelow, the substituents and symbols have the same meaning as described under formula (I), unless otherwise defined.

In formula (I) and all subsequent formulae, linear carbon-containing radicals such as alkyl, alkoxy, haloalkyl, haloalkoxy, alkylamino and alkylthio, and the corresponding unsaturated and/or substituted radicals can be in each case straight-chain or branched in the carbon skeleton, such as alkenyl and alkynyl. Unless specifically stated, the lower carbon skeletons, for example those having 1 to 6 carbon atoms, or in the case of unsaturated groups, having 2 to 4 carbon atoms, are preferred amongst these radicals. Alkyl radicals, also in the composite meanings such as alkoxy, haloalkyl and the like, are, for example, methyl, ethyl, n- or i-propyl, n-, i-, t- or 2-butyl, pentyls, hexyls, such as n-hexyl, i-hexyl and 1,3-dimethylbutyl, heptyls such as n-heptyl, 1-methylhexyl and 1,4-dimethylpentyl; alkenyl- and alkynyl radicals have the meanings of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl. The multiple bond can be located in any position of the unsaturated radical.

Unless specifically stated, cycloalkyl is a carbocyclic saturated ring system having three to eight carbon atoms, for example cyclopropyl, cyclopentyl or cyclohexyl.

Analogously, cycloalkenyl is a monocyclic alkenyl group having three to eight carbon ring members, for example cyclopentyl, cyclobutenyl, cyclpentyl and cyclohexenyl, it being possible for the double bond to be located in any position.

In the case of a disubstituted amino group, such as dialkylamino, these two substituents can be identical or different.

Halogen is fluorine, chlorine, bromine or iodine. Haloalkyl, -alkenyl and -alkynyl are alkyl, alkenyl or alkynyl, each of which is partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; the same applies analogously to haloalkenyl and other halogen-substituted radicals.

The term heterocyclyl is to be understood as meaning the radicals of three- to nine-membered, saturated, partially or fully unsaturated heterocycles which contain one to three hetero atoms selected from the group consisting of oxygen, nitrogen and sulfur. If chemically possible, the linkage may be effected at any position of the heterocycle. Heterocyclyl is preferably aziridinyl, oxiranyl, tetrahydrofuranyl, tetrahydropyranyl, tetrahydrothienyl, pyrrolidinyl, isoxazolidinyl, isoxazolinyl, thiazolinyl, thiazolidinyl, pyrazolidinyl, morpholinyl, piperidinyl, dioxolanyl, dioxanyl, piperazinyl, oxepanyl, azepanyl.

Heteroaryl is the residue of a heteroaromatic ring which, besides carbon ring members, contains one to five hetero atoms selected from the group consisting of nitrogen, oxygen and sulfur. Heteroaryl is preferably furanyl, thienyl, pyrrolyl, pyrazolyl, imidazolyl, oxazolyl, thiazolyl, isoxazolyl, isothiazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,2,3-thiadiazolyl, 1,2,4-thiadiazolyl, 1,2,5-thiadiazolyl, 1,3,4-thiadiazolyl, tetrazolyl, pyridyl, pyridazinyl, pyrimidinyl, pyrazinyl, 1,2,4-triazinyl, 1,3,5-triazinyl.

Aryl represents an aromatic mono- or polycyclic hydrocarbon radical, for example phenyl, naphthyl, biphenyl and phenanthryl.

Examples of a radical $AB(C)_q(D)_o$ are: naphthyridine, phenanthroline, quinoline, pyrazino[2,3-c]pyridazine, 1H-pyrrolo[2,3-b]pyridine, 4,8b-dihydro-3aH-indeno[2,1-d]isoxazole, 4,5,6,7-tetrahydrobenzothiazole, 3-oxa-4-azatricyclo[5.2.1.0$^{2,6}$]dec-4-ene, 4,8b-dihydro-3aH-indeno[2,1-d]isoxazole, 3a,4,6,6a-tetrahydrofuro[3,4-d]isoxazole, 3a,4,5,6a-tetrahydrofuro[3,2-d]isoxazole, 3a,4,5,6,7,7a-hexahydrobenzo[d]isoxazole, 4,5,6,7,8,8a-hexahydro-3aH-cyclohepta[d]isoxazole, 4,5,6,6a-tetrahydro-3aH-cyclopenta[d]isoxazole, 5,6-dihydro-4H-cyclopenta[b]furan, 4,5,6,7-tetrahydrobenzo[d]isoxazole, 5,6-dihydro-4H-cyclopenta[b]thiophene, 2,3-dihydrothieno[2,3-b]thiophene and 5,6-dihydro-4H-thieno[2,3-b]thiopyran.

If a group or a radical is polysubstituted, this is to be understood as meaning that the general principles of the construction of chemical compounds must be taken into consideration when combining the various substituents, i.e. it must be avoided that compounds are formed which are known to the skilled worker to be chemically unstable or not possible. This also applies analogously to the linkages of individual radicals.

If a group or a radical is polysubstituted by other radicals, these other radicals can be identical or different. If a heterocyclic radical is substituted by hydroxyl, this definition is also understood as encompassing the tautomeric form of the oxo group.

Depending on the type and linkage of the substituents, the compound of the formula (I) can exist as stereoisomers. If, for example, one or more alkenyl groups are present, diastereomers may occur. If, for example, one or more asymmetric carbon atoms are present, enantiomers and diastereomers may occur. Stereoisomers may be obtained from the mixtures obtained upon preparation by customary separation methods, for example by chromatographic separation methods. Likewise, stereoisomers can be prepared selectively by employing stereoselective reactions using optically active starting materials and/or auxiliaries. The invention also relates to all stereoisomers and mixtures thereof which are encompassed by the formula (I), but not specifically defined.

For the choice of the meanings of "Y" and "Z", "Y" and "Z" shall not simultaneously represent in each case one divalent hetero atom unit.

Compounds of the formula I which are of greater interest are those in which $R^1$ is chlorine, bromine, methyl, ethyl, cyano, nitro, halogen-$(C_1-C_2)$-alkyl, $(C_1-C_2)$-alkylthio, $(C_1-C_2)$-alkylsulfinyl or $(C_1-C_2)$-alkylsulfonyl;

$R^5$ is $(C_1-C_4)$-alkyl, $(C_3-C_8)$-cycloalkyl, $(C_1-C_4)$-alkoxy, $(C_1-C_4)$-alkoxy-$(C_1-C_4)$-alkyl, $(C_1-C_4)$-alkylcarbonyl, $(C_1-C_4)$-alkoxycarbonyl, $(C_1-C_4)$-alkylthio, phenyl, or two radicals $R^5$ bonded to a joint carbon atom form a chain selected from the group consisting of $OCH_2CH_2O$, $OCH_2CH_2CH_2O$, $SCH_2CH_2S$ and $SCH_2CH_2CH_2S$, this being substituted by w methyl groups, or two radicals $R^5$ bonded to directly adjacent carbon atoms form a bond or together with the carbon atoms to which they are attached form a 3- to 6-membered ring which is substituted by w radicals selected from the group consisting of halogen, $(C_1-C_4)$-alkyl, $(C_1-C_4)$-alkylthio and $(C_1-C_4)$-alkoxy, and $R^9$ is a radical of the formula Va to Vt.

Compounds of the formula I which are of particular interest are those in which $R^3$ is halogen, halogen-$(C_1-C_2)$-alkyl, $(C_1-C_2)$-alkylsulfenyl, $(C_1-C_2)$-alkylsulfinyl, $(C_1-C_2)$-alkylsulfonyl or nitro;

$R^7$ is hydrogen, $(C_1-C_4)$-alkylsulfonyl, benzoyl or phenylsulfonyl, the two last-mentioned groups being substituted by v radicals selected from the group consisting of $(C_1-C_2)$-alkyl, halogen-$(C_1-C_2)$-alkyl, $(C_1-C_2)$-alkoxy, halogen-$(C_1-C_2)$-alkoxy, halogen, cyano and nitro, and $R^{11}$ is hydrogen, $(C_1-C_4)$-alkyl, $(C_2-C_4)$-alkenyl, $(C_2-C_4)$-alkynyl or $(C_3-C_8)$-cycloalkyl.

Preferred compounds of the formula I are those in which $R^4$ is $OR^7$, $(C_1-C_4)$-alkylthio, $(C_1-C_4)$-alkylsulfonyl, cyano, cyanato, thiocyanato, or is phenylthio which is substituted by v radicals selected from the group consisting of halogen, $(C_1-C_2)$-alkyl, $(C_1-C_2)$-alkoxy, halogen-$(C_1-C_2)$-alkyl, halogen-$(C_1-C_2)$-alkoxy and Nitro;

$R^5$ is $(C_1-C_4)$-alkyl, $(C_3-C_8)$-cycloalkyl, $(C_1-C_4)$-alkoxy, $(C_1-C_4)$-alkylthio, phenyl, or two radicals $R^5$ bonded to directly adjacent carbon atoms together with the carbon atoms to which they are attached form a substituted 3- to 6-membered ring;

$R^{12}$ is hydrogen, $(C_1-C_4)$-alkyl, $(C_2-C_4)$-alkenyl, or, if $R^{11}$ and $R^{12}$ are bonded to one atom or to two directly adjacent atoms, they form together with the atoms binding them a saturated, partially or fully unsaturated five- to six-membered ring which contains p hetero atoms selected from the group consisting of oxygen, nitrogen and sulfur;

Y is a divalent unit selected from the group consisting of O, N—H, N—$(C_1-C_4)$-alkyl, $CHR^5$ and $C(R^5)_2$, and Z is a divalent unit selected from the group consisting of O, S, $SO_2$, N—$(C_1-C_4)$-alkyl, $CHR^5$ and $C(R^5)_2$.

Compounds of the formula I which are likewise preferred are those in which $R^3$ is halogen, halogen-$(C_1-C_2)$-alkyl or $(C_1-C_2)$-alkylsulfonyl;

$R^7$ is hydrogen, $(C_1-C_4)$-alkylsulfonyl, benzoyl or phenylsulfonyl, and $R^8$ is hydrogen, methyl, ethyl or halogen.

Especially preferred compounds of the formula I are those in which $R^4$ is $OR^7$, $(C_1-C_4)$-alkylthio or phenylthio;

$R^5$ is $(C_1-C_4)$-alkyl, or two radicals $R^5$ bonded to directly adjacent carbon atoms together with the carbon atoms to which they are attached form a substituted 3- to 6-membered ring;

$R^9$ is a radical of the formula Va to Ve;

Y is a divalent unit selected from the group consisting of N—$(C_1-C_4)$-alkyl, $CHR^5$ and $C(R^5)_2$, and Z is a divalent unit selected from the group consisting of $CHR^5$ and $C(R^5)_2$.

Very especially preferred compounds of the formula I are those in which $R^1$ and $R^3$ in each case independently of one another are chlorine, bromine, methyl, methylsulfonyl, ethylsulfonyl, trifluoromethyl, cyano or nitro;

$R^4$ is hydroxyl;

$R^5$ is methyl;

$R^6$ is cyanomethyl, methoxymethyl, ethoxymethyl, methylsulfenylmethyl, methylsulfinylmethyl, methylsulfonylmethyl, ethylsulfenylmethyl, ethylsulfinylmethyl, ethylsulfonylmethyl;

$R^7$ is hydrogen, $(C_1-C_4)$-alkylsulfonyl, benzoyl or phenylsulfonyl, and $R^8$ is hydrogen, methyl, ethyl or halogen;

$R^9$ is a radical of the formula Va to Ve;

$R^{11}$ is hydrogen, $(C_1-C_4)$-alkyl, $(C_2-C_4)$-alkenyl, $(C_2-C_4)$-alkynyl or $(C_3-C_8)$-cycloalkyl p is 1;

v is 0, 1, or 2;

w is 0, 1, or 2 and

Y and Z independently of one another are $CH_2$, and $AB(C)_q(D)_o$ is 4,5-dihydroisoxazol-3-yl.

Depending on the meaning of the substituents, the compounds according to the invention can be prepared for example by one or more of the processes shown in the schemes which follow.

Compounds of the formula (Ia) according to the invention can be prepared in a two-step process by reacting a cyclohexanedione of the formula (II) with a benzoyl derivative of the formula (III) in which I represents halogen, as shown in Scheme 1.

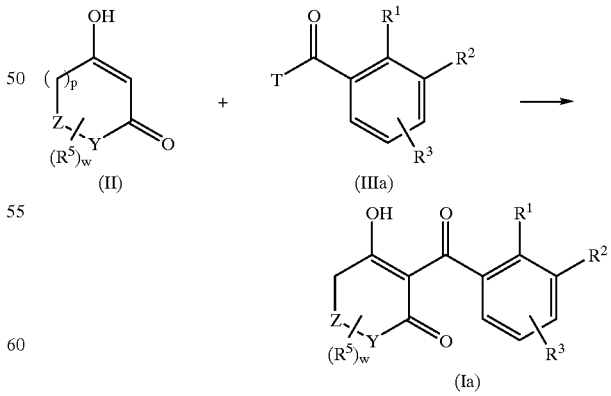

The first step of the reaction sequence, the acylation, is carried out in a generally known fashion, for example by adding an acid chloride of the formula (IIIa) in which T is chlorine to the solution or suspension of the cyclohexane- 1,3-dione (II) in the presence of an auxiliary base. The reactants and the auxiliary base are expediently employed in equimolar amounts. A small excess, for example 1.2 to 1.5 mol equivalents, of the auxiliary base based on (II) may be advantageous.

Auxiliary bases which are suitable are, for example, tertiary alkylamines, pyridine or alkali metal carbonates. Solvents which can be used are, for example, methylene chloride, diethyl ether, toluene or ethyl acetate.

During addition of the acid chloride, the reaction mixture is preferably cooled to 0 to 10° C., and the mixture is then stirred at a temperature of 20 to 100° C., in particular 25 to 50° C., until the reaction has ended. Work-up is carried out in a manner known per se, for example the reaction mixture is poured into water and any product is extracted with methylene chloride. After the organic phase has been dried and the solvent has been removed, the crude enol ester can be employed without further purification in the rearrangement reaction. Preparation examples of benzoyl enol esters of cyclohexane-1,3-dione are described, for example, in EP-A 186 118 or U.S. Pat. No. 4,780,127.

Rearrangement of the enol esters to give the compounds of the formula (I) according to the invention is expediently carried out at temperatures from 20° C. to 40° C. in solvent and in the presence of an auxiliary base and with the aid of a cyano compound as catalyst.

Solvents which can be employed are, for example, acetonitrile, methylene chloride, 1,2-dichlorethane, ethyl acetate or toluene. The preferred solvent is acetonitrile. Suitable as auxiliary base are tertiary alkylamines, pyridine or alkali metal carbonates, all of which are preferably employed in an equimolar amount or in an up to fourfold excess based on the benzoyl enol ester. The preferred auxiliary base is triethylamine in double quantity.

Suitable catalysts are, for example, potassium cyanide or acetone cyanohydrin, preferably in an amount of 1 to 50 mol %, based on the enol ester. Preferably, acetone cyanohydrin is added, for example in an amount of 5 to 15, in particular 10, mol %. Examples of such cyanide-catalyzed rearrangements of enol esters of the cyclohexane 1,3-diones are described, for example, in EP-A 186 118 or U.S. Pat. No. 4,780,127.

Work-up is carried out in a manner known per se. For example, the reaction mixture is acidified with dilute mineral acids such as 5% strength hydrochloric acid or sulfuric acid, and extracted with an organic solvent such as methylene chloride or ethyl acetate, the end product passing into the aqueous phase. Acidification of the aqueous solution results in the product according to the invention being precipitated or reextracted with methylene chloride, dried and subsequently freed from solvent.

The 1,3-diketones of the formula (II) used as starting material are known or can be prepared by processes known per se (cf. EP-A 71 707, EP-A 142 741, EP-A 243 313, U.S. Pat. No. 4,249,937 and WO 92/13821).

Compounds of the abovementioned formula (IIIa) can be prepared by methods known per se from compounds of the formula (IIIb) in which T is hydroxyl. For example, compounds of the formula (IIIb) can be prepared from compounds of the formula (IIIc), in which T is $(C_1–C_4)$-alkoxy by means of acidic or basic hydrolysis. Compounds of the formula (IIIc) can be prepared for example in accordance with the method described in Scheme 2.

Scheme 2

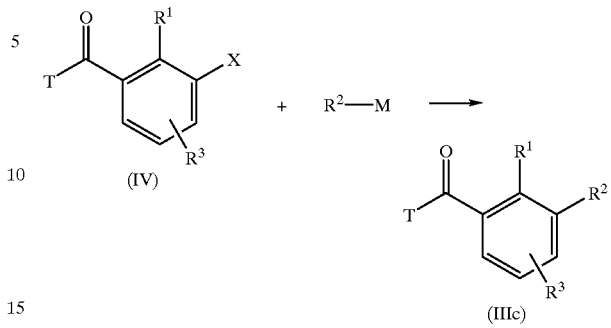

In this scheme, X is chlorine, bromine, iodine, trifluoromethylsulfonyloxy or fluorosulfonyloxy, and M is $Sn(C_1–C_4\text{-alkyl})_3$, $B(OH)_2$ or ZnHal. In accordance with Scheme 2, the aromatic halogen and sulfonyloxy compounds (IV) are reacted in a manner known per se with heteroaryl stannates (Stille Coupling), heteroaryl-boron compounds (Suzuki coupling) or heteroaryl-zinc compounds (Negishi reaction) of the formula $R^2$-M in the presence of a palladium or nickel catalyst and, if appropriate, of a base; cf., for example Synthesis 1987, 51–53, Synthesis 1992, 413).

Compounds of the formula (IIIb) and (IIIc) can also be prepared from compounds of the formula (V), for example in accordance with the method described in Scheme 3.

Scheme 3

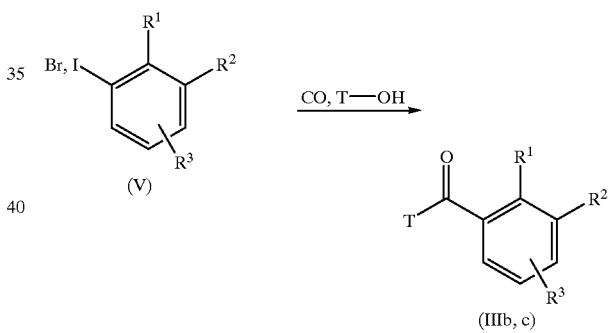

In this scheme, the compounds of the formula (V) are reacted with carbon monoxide and water under elevated pressure in the presence of a palladium, nickel, cobalt or rhodium catalyst and of a base.

Compounds of the formula (I) according to the invention in which $R^4$ is other than hydroxyl can be prepared for example in accordance with Scheme 4. The reaction shown therein of a compound of the formula (Ia) with a halogenating reagent such as oxalyl chloride or oxalyl bromide leads to compounds of the formula (Ib) according to the invention which can be reacted into further compounds of the formula (Ic) according to the invention in which $R^4$ is alkylthio, haloalkylthio, alkenylthio, haloalkenylthio, alkynylthio, haloalkinylthio, unsubstituted or substituted phenylthio, cyano, cyanato, thiocyanato or $OR^7$ by reaction with nucleophiles such as alkali metal cyanides, alkali metal cyanates, alkali metal thiocyanates, alkylthio alcohols thiophenols, if appropriate with base catalysis. Such reactions are described, for example, in Synthesis 12, 1287 (1992). A reaction with an oxidant such as m-chloroperoxybenzoic acid, peroxyacetic acid, hydrogen peroxide and potassium peroxymonosulfate results in compounds of the formula (Ic) according to the invention in which $R^4$ is alkylsulfinyl, haloalkylsulfinyl, alkenylsulfinyl, haloalkenylsulfinyl, alkynylsulfinyl, haloalkynylsulfinyl, alkylsulfonyl, haloalkylsulfonyl, alkenylsulfonyl, haloalkenylsulfonyl, alkynylsulfonyl, unsubstituted or substituted phenylthio or haloalkynylsulfonyl. Such reactions are described, for example, in *J. Org. Chem.* 53, 532 (1988), *Tetrahedron Lett.* 21, 1287 (1981).

Scheme 4

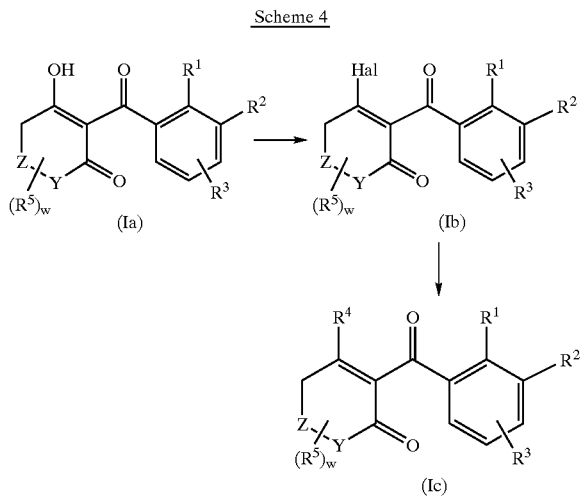

The abovementioned nickel, cobalt, rhodium and, in particular, palladium catalysts can be in metal form or in the form of customary salts, such as in the form of halogen compounds, for example $PdCl_2$, $RhCl_3 \cdot H_2O$, acetates, for example Pd $(OAc)_2$, cyanides and the like at the known valence states. Metal complexes with tertiary phosphines, metal alkyl carbonyls, metal carbonyls, for example $Co_2(CO)_8$, $Ni(CO)_2$, metal carbonyl complexes with tertiary phosphines, for example $(PPh_3)_2Ni(CO)_2$, or transition metal salts complexed with tertiary phosphines may furthermore be present. The last-mentioned embodiment is particularly preferred when palladium is used as the catalyst. The type of the phosphine ligands can be varied within wide limits. For example, they can be represented by the following formulae:

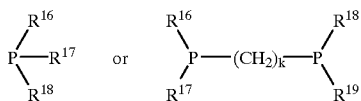

In this context, k denotes the numbers 1, 2, 3, or 4, and the radicals $R^{16}$ to $R^{19}$ are carbon-containing radicals such as $(C_1–C_6)$-alkyl, aryl, $(C_1–C_4)$-alkylaryl, such as benzyl, phenethyl or aryloxy. Aryl is, for example, naphthyl, anthryl and, preferably, substituted or unsubstituted phenyl; as regards the substituents, care must be taken only that they are inert to the carboxylation reaction, otherwise they can be varied within wide limits and comprise all inert carbon-organic radicals such as COOH, COOM (M is, for example, an alkali metal salt, alkaline earth metal salt or ammonium salt), or carbon-organic radicals which are bonded via oxygen, such as $(C_1–C_6)$-alkoxy radicals.

The phosphine complexes can be produced in a manner known per se, for example as described in the documents mentioned at the outset. For example, customary commercially available metal salts such as $PdCl_2$ or $Pd(OCOCH_3)_2$ are used as starting materials, and the phosphine, for example $P(C_6H_5)_3$, $P(n-C_4H_9)_3$, $PCH_3(C_6H_5)_2$, 1,2-bis(diphenylphosphino)ethane is added.

The amount of transition metal is less critical. Naturally, a smaller amount, for example from 0.1 to 10 mol %, in particular 1 to 5 mol %, based on the starting material (II) or (III) will be used, also for financial reasons.

To prepare the benzoic acids (IIIc), the reaction is carried out with carbon monoxide and at least equimolar amounts of water, based on the starting materials (IV). The reactant water can simultaneously also act as the solvent.

However, depending on the nature of the starting materials and of the catalysts used, it may also be advantageous to use another inert solvent instead of the reactant, or to use the base employed for the carboxylation as the solvent.

Suitable inert solvents for carboxylation reactions are customary solvents such as hydrocarbons, for example toluene, xylene, hexane, pentane, cyclohexane, ethers, for example methyl t-butyl ether, tetrahydrofuran, dioxane, dimethoxyethane, substituted amides such as dimethylformamide, persubstituted ureas such as tetra-$(C_1–C_4)$-alkylureas, or nitriles such as benzonitrile or acetonitrile.

In a preferred embodiment of the process, one of the reactants, in particular the base, is used in an excess so that no additional solvent is required.

Bases which are suitable for the process are all inert bases which are capable of binding the hydrogen iodide or hydrogen bromide which is liberated during the reaction. Examples which may be mentioned in this context are tertiary amines such as tert-alkylamines, for example trialkylamines such as triethylamine, cyclic amines such as N-methylpiperidine or N,N'-dimethylpiperazine, pyridine, alkali metal carbonates or alkali metal hydrogen carbonates, or tetraalkyl-substituted urea derivatives such as tetra-$(C_1–C_4)$-alkylurea, for example tetramethylurea.

As a rule, the amount of base can be varied within wide ranges, 1 to 10, in particular 1 to 5, mol usually being used. When the base is simultaneously used as the solvent, the amount chosen will, as a rule, be such that the reactants are dissolved, while unnecessarily high excesses are avoided for practical reasons in order to save costs, to be able to employ small reaction vessels and to ensure maximum contact between the reactants.

During the reaction, the carbon monoxide pressure is set in such a way that an excess of CO based on (IV) is always present. The carbon monoxide pressure at room temperature is preferably 1 to 250 bar, in particular 5 to 150 bar, CO.

As a rule, the carbonylation reaction is carried out at temperatures of 20 to 250° C., in particular 30 to 150° C., either continuously or batchwise. In the case of batchwise operation, it is expedient continuously to inject carbon monoxide above the reaction mixture in order to maintain a constant pressure.

The arylhalogen compounds (IV) used as starting compounds are known or can be prepared readily by a suitable combination of known syntheses.

For example, the halogen compounds (IV) can be obtained by a Sandmeyer reaction from suitable anilines which, in turn, are synthesized by reducing suitable nitro compounds (cf., for example, Liebigs Ann. Chem. 1980, 768–778). Moreover, the aryl bromides (IV) can be obtained by directly brominating suitable starting compounds [cf., for example Monatsh. Chem. 99, 815–822 (1968)].

The compounds of the formulae (IVa) to (IVm) shown in schemes 4 and 5 are particularly suitable for the preparation of the heterocyclic compounds of the formula (IIIa,b,c).

In these schemes, the symbols have the following meanings:

$R^{20}$ is hydrogen, $C_1–C_4$-alkyl, $C_1–C_4$-haloalkyl, $C_3–C_8$-cycloalkyl, substituted or unsubstituted phenyl or trimethylsilyl, $R^{21}$ is hydrogen, $C_1$–$C_4$-haloalkyl, $C_3$–$C_8$-cycloalkyl or substituted or unsubstituted phenyl.

Starting from the arylhalogen compounds or arylsulfonates, aryl methyl ketones (IVa) can be prepared by processes known from the literature in the presence of a palladium or nickel transition metal catalyst and, if appropriate, in the presence of a base by reaction with vinyl alkyl ethers followed by hydrolysis [cf., for example, Tetrahedron Lett. 32, 1753–1756 (1991)].

The ethynylated aromatic compounds (IVb) can be prepared in a manner known per se by reacting arylhalogen compounds or arylsulfonates (IV) with substituted acetylenes in the presence of a palladium or nickel transition metal catalyst (for example Heterocycles, 24, 31–32 (1986)). Derivatives (IVb) with $R^{20}$=H are expediently obtained from the silyl compounds (IVb), $R^{20}$=—Si(CH$_3$)$_3$ [J. Org. Chem. 46, 2280–2286 (1981)].

The arylalkenes (IVc) are obtained by subjecting arylhalogen compounds or arylsulfonates (IV) and olefins to a Heck reaction in the presence of a palladium catalyst (cf., for example, Heck, Palladium Reagents in Organic Synthesis, Academic Press, London 1985 or Synthesis 1993, 735–762).

The benzoyl derivatives (IV) used as starting compounds are known [cf., for example, Coll. Czech. Chem. Commn. 40, 3009–3019 (1975)] or can be prepared readily by combining known syntheses in a suitable manner.

For example, the sulfonates (IV) (X=—OS(O)$_2$CF$_3$, —OS(O)$_2$F) can be obtained from the corresponding phenols, which, in turn, are known (cf., for example EP 195247) or can be prepared by known methods (cf., for example Synthesis 1993, 735–762).

The halogen compounds (IV) (X=Cl, Br or I) can be obtained for example from suitable anilines by Sandmeyer reaction.

Scheme 5

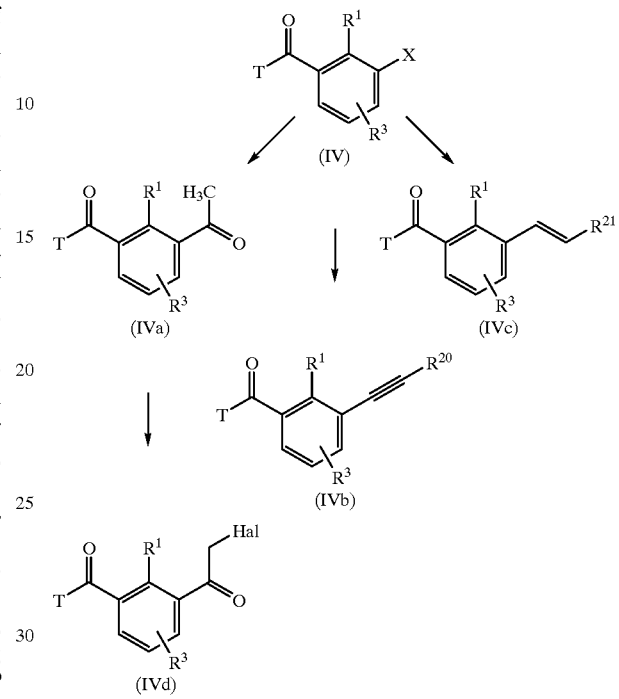

Scheme 6

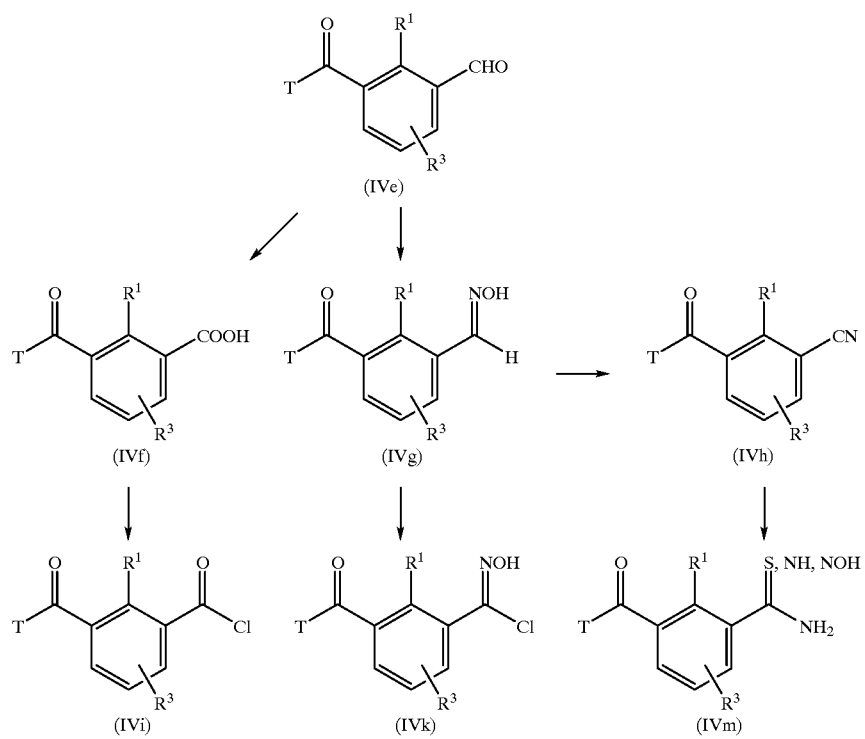

Isophthalic acid derivatives (IVf) can be prepared from the aldehydes (IVe) by known processes [see J. March Advanced Organic Chemistry 3$^{rd}$ Ed, p. 629 et seq., Wiley-Interscience Publication (1985)].

The oximes (IVg) are advantageously obtained by reacting aldehydes (IVe) with hydroxylamine in a manner known per se [(see for example: J. March Advanced Organic Chemistry 3rd Ed., pp. 805–806, Wiley-Interscience Publication (1985)].

Likewise, the conversion of the oximes (IVg) into nitriles (IVh) can be carried out by methods known per se [see J. March Advanced Organic Chemistry 3rd Ed., pp. 931–932, Wiley-Interscience Publication (1985)].

The aldehydes (IVe) required as starting compounds are known or can be prepared by known methods. For example, they can be synthesized from the methyl compound (VI) in accordance with Scheme 6.

Scheme 7

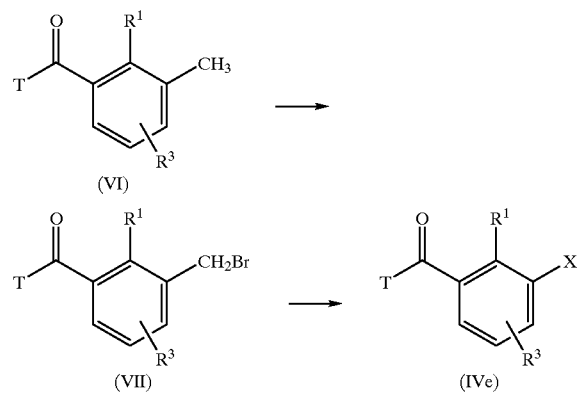

The methyl compounds (VI) can be reacted by generally known methods, for example with N-bromosuccinimide or 1,3-dibromo-5,5-dimethylhydantoin, to give the benzaldehydes (IVe). The reaction of benzyl bromides to give benzaldehydes (IVe) is likewise known from the literature [cf. Synth. Commun. p. 22 1967–1971 (1992)].

The precursors (IVa) to (IVh) are suitable for synthesizing heterocyclic intermediates III.

For example, bicyclic 5-oxazolyl derivatives [cf., for example, J. Heterocyclic Chem., 28, pp. 17–28 (1991)] or bicyclic 4-thiazolyl derivatives [cf., for example Metzger, Thiazoles in: The Chemistry of Heterocyclic Compounds, Vol. 34 p. 175 et seq. (1976)] can be obtained from the acetophenones (IVa) via the halogenated intermediate (IVd).

The acetylenes (IVb) or the alkenes (IVc) are suitable for synthesizing bicyclic 4-isoxazolyl, 5-isoxazolyl, 4,5-dihydroisoxazol-4-yl, 4,5-dihydroisoxazol-5-yl derivatives [cf., for example, Houben-Weyl, Methoden der organischen Chemie [Methods in Organic Chemistry], 4th Ed., Vol. X/3, p. 843 et seq. (1965)].

Bicyclic 1,2,4-triazol-3-yl derivatives can be prepared from benzonitriles (IVh) by known methods [cf., for example, J. Chem. Soc. 3461–3464 (1954)].

The benzonitriles (IVh) can be converted into bicyclic 1,2,4-oxadiazol-3-yl derivatives [cf., for example, J. Heterocyclic Chem., 28, 17–28 (1991)], 2-thiazolyl derivatives, 4,5-dihydrothiazol-2-yl derivatives or 5,6-dihydro-4H-1,3-thiazin-2-yl derivatives [cf. Houben Weyl, Methoden der organischen Chemie, 4th Ed., Vol. E5, p. 1268 et seq. (1985)] via the intermediate of the thioamides, amide oximes or amidines (IVm). Bicyclic 1,2,4-thiadiazol-5-yl derivates [cf., for example, J. Org. Chem. 45 3750–3753 (1980)] or bicyclic 1,3,4-thiadiazol-2-yl derivatives [cf., for example, J. Chem.Soc., Perkin Trans. I 1987–1991 (1982)] are likewise obtainable from the thioamides (IVm) by processes known from the literature.

The conversion of oximes (IVg) into 3-isoxazolyl derivatives can be effected in a manner known per se via the intermediate hydroxamyl chlorides (IVk) [cf., for example, Houben Weyl, Methoden der organischen Chemie, 4th Ed., Vol. X/3, p. 843 et seq. (1965)].

Compounds of the formulae (IIIa), (IIIb) and (IIIc) are novel and likewise subject of the invention.

The compounds of the formula (I) according to the invention have an outstanding herbicidal activity against a broad spectrum of economically important monocotyledonous and dicotyledonous harmful plants. The active ingredients also act efficiently on perennial weeds which produce shoots from rhizomes, rootstocks or other perennial organs and which are difficult to control. In this context, it does not matter whether the substances are applied before sowing, pre-emergence or post-emergence. Specific examples may be mentioned of some representatives of the monocotyledonous and dicotyledonous weed flora which can be controlled by the compounds according to the invention, without the enumeration being a restriction to certain species. Examples of weed species on which the herbicidal compositions act efficiently are, from amongst the monocotyledonous weed species, Avena, Lolium, Alopecurus, Phalaris, Echinochloa, Digitaria, Setaria and Cyperus species, in particular Setaria species, from the annual group, and, among the perennial species, Agropyron, Cynodon, Imperata and Sorghum and also perennial Cyperus species.

In the case of the dicotyledonous weed species, the spectrum of action extends to genera such as, for example, Galium, Viola, Veronica, Lamium, Stellaria, Amaranthus, Sinapis, Ipomoea, Sida, Matricaria and Abutilon amongst the annuals, and Convolvulus, Cirsium, Rumex and Artemisia in the case of the perennial weeds. The active ingredients according to the invention also act outstandingly efficiently on harmful plants which are found under the specific cultures in rice, such as, for example, Echinochloa, Sagittaria, Alisma, Eleocharis, Scirpus and Cyperus. If the compounds according to the invention are applied to the surface before germination, the weed seedlings are either prevented completely from emerging or else the weeds grow until they have reached the cotyledon stage, but then their growth stops, and, eventually, after three to four weeks have elapsed, they die completely. If the active ingredients are applied post-emergence to the green parts of the plants, growth likewise stops drastically a very short time after the treatment, and the weed plants remain at the growth stage of the point of time of application, or they die completely after a certain time, so that in this manner competition by the weeds, which is harmful to the crop plants, is eliminated very early and in a sustained manner.

Even though the compounds according to the invention have an outstanding herbicidal activity against undesired monocotyledonous and dicotyledonous harmful plants, in particular Setaria species, crop plants of economically important crops such as, for example, wheat, barley, rye, rice, sugarbeet, soybean and, in particular, cotton and maize, are harmed only to a minor extent, if at all. For these reasons, the present compounds are highly suitable for the selective control of undesired vegetation in stands of agriculturally useful plants or of ornamentals.

Owing to their herbicidal and plant-growth regulatory properties, the active ingredients can also be employed for controlling harmful plants in crops of genetically modified plants which are known or yet to be developed. As a rule, the transgenic plants are distinguished by particular advantageous properties, for example by resistances to certain pesticides, especially certain herbicides, resistances to plant diseases or to plant pathogens such as certain insects or microorganisms such as fungi, bacteria or viruses. Other particular properties concern for example the harvested material with regard to quantity, quality, storeability, composition and specific constituents. Thus, transgenic plants with an increased starch content or with a modified starch quality or with a different fatty acid composition of the harvested material are known.

The compounds of the formula (I) according to the invention or their salts in economically important transgenic crops of useful plants and ornamentals, such as of cereals such as wheat, barley, rye, oats, sorghum and millet, rice, cassava and maize or else crops of sugarbeet, cotton, soybean, oilseed rape, potato, tomato, pea and other vegetables is preferred. The compounds of the formula (I) may preferably be employed as herbicides in crops of useful plants which are resistant to the phytotoxic effects of the herbicides or which have been rendered resistant to the phytotoxic effects of the herbicides by recombinant means.

Conventional methods of generating novel plants which have modified properties in comparison to plants occurring to date consists, for example, in traditional breeding methods and the generation of mutants. Alternatively, novel plants with modified properties can be generated with the aid of recombinant methods (see, for example. EP-A-0221044, EP-A-0131624). For example, the following have been described in several cases:

the modification, by recombinant technology, of crop plants with the aim of modifying the starch synthesized in the plants (for example WO 92/11376, WO 92/14827, WO 91/19806), transgenic crop plants which are resistant to certain herbicides of the type glufosinate (cf., for example, EP-A-0242236, EP-A-242246) or glyphosate (WO 92/00377) or of the sulfonylureas (EP-A-0257993, U.S. Pat. No. 5,013,659), transgenic crop plants, for example cotton, with the capability of producing *Bacillus thuringiensis* toxins (Bt toxins), which make the plants resistant to certain pests (EP-A-0142924, EP-A-0193259), transgenic crop plants with a modified fatty acid composition (WO 91/13972).

A large number of molecular biological techniques are known in principle with the aid of which novel transgenic plants with modified properties can be generated; see, for example, Sambrook et al., 1989, Molecular Cloning, A Laboratory Manual, 2nd Ed., Cold Spring Harbor Laboratory Press, Cold Spring Harbor, N.Y.; or Winnacker "Gene und Klone" [Genes and Clones], VCH Weinheim 2nd Edition 1996, or Christou, "Trends in Plant Science" 1 (1996) 423–431).

To carry out such genetic manipulations, nucleic acid molecules which allow mutagenesis or sequence changes by recombination of DNA sequences can be introduced into plasmids. For example, the abovementioned standard methods allow base exchanges to be carried out, subsequences to be removed, or natural or synthetic sequences to be added. To connect the DNA fragments to each other, adapters or linkers may be added to the fragments.

For example, the generation of plant cells with a reduced activity of a gene product can be achieved by expressing at least one corresponding antisense RNA, a sense RNA for achieving a cosuppression effect or by expressing at least one suitably constructed ribozyme which specifically cleaves transcripts of the abovementioned gene product.

To this end, it is possible to use, on the one hand, DNA molecules which encompass the entire coding sequence of the gene product inclusive of any flanking sequences which may be present, as well as DNA molecules which only encompass portions of the coding sequence, it being necessary for these portions to be long enough to have an antisense effect on other cells. The use of DNA sequences which have a high degree of homology to the coding sequences of a gene product, but which are not completely identical to them, is also possible.

When expressing nucleic acid molecules in plants, the protein synthesized can be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219–3227; Wolter et al., Proc. Natl. Acad. Sci. USA 85 (1988), 846–850; Sonnewald et al., Plant J. 1 (1991), 95–106).

The transgenic plant cells can be regenerated by known techniques to give rise to intact plants. In principle, the transgenic plants can be plants of any desired species, i.e. both monocots and dicots.

Thus, transgenic plants can be obtained whose properties are altered by overexpression, suppression or inhibition of homologous (=natural) genes or gene sequences or the expression of heterologous (=foreign) genes or gene sequences.

The compounds according to the invention can preferably be employed in transgenic crops which are resistant to herbicides from the group of the sulfonylureas, glufosinate-ammonium or glyphosate-isopropylammonium and analogous active ingredients.

When the active ingredients according to the invention are used in transgenic crops, effects are frequently observed, in addition to the effects against harmful plants observed in other crops, which are specific for the application in the transgenic crop in question, for example a modified or specifically extended weed spectrum which can be controlled, altered application rates which can be employed for application, preferably good combining properties with the herbicides to which the transgenic crop is resistant, and an effect on growth and yield of the transgenic crop plants. A subject of the invention is therefore also the use of the compounds according to the invention as herbicides for controlling harmful plants in transgenic crop plants.

Moreover, the substances according to the invention have outstanding growth-regulatory properties in crop plants. They engage in the plants' metabolism in a regulatory manner and can thus be employed for provoking directed effects on plant constituents and to facilitate harvesting, such as, for example, by triggering desiccation and stunted growth. Moreover, they are also suitable for the general control and inhibition of undesired vegetative growth without simultaneously destroying the plants. An inhibition of vegetative growth is very important in a large number of monocotyledonous and dicotyledonous crops since lodging can thus be reduced, or prevented completely.

The compounds according to the invention can be applied in the form of wettable powders, emulsifiable concentrates, sprayable solutions, dusts or granules in the customary preparations. A subject of the invention are therefore also herbicidal and plant-regulatory compositions which comprise the compounds of the formula (I).

The compounds of the formula (I) can be formulated in many ways, depending on the biological and/or chemico-physical parameters which prevail. The following are examples of possibilities for formulations: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusts (DP), seed-dressing materials, granules for broadcasting and soil application, granules (GR) in the form of microgranules, spray granules, coated granules and adsorption granules, water-dispersible granules (WG), water-soluble granules (SG), ULV formulations, microcapsules and waxes. These individual formulation types are known in principle and are described, for example, in Winnacker-Küchler, "Chemische Technologie" [Chemical Engineering], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives, are also known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", [Surface-active ethylene oxide adducts], Wiss. Verlagsgesell., Stuttgart 1976; Winnacker-Küchler, "Chemische Technologie", Volume 7, C. Hauser Verlag Munich, 4th Edition 1986.

Wettable powders are products which are uniformly dispersible in water and which, besides the active ingredient, also comprise ionic or nonionic surfactants (wetters, dispersants), for example polyoxyethylated alkylphenols, polyethoxylated fatty alcohols, polyethoxylated fatty amines, fatty alcohol polyglycol ether sulfates, alkanesulfonates, alkylbenzenesulfonates, sodium 2,2'-dinaphthylmethane-6,6'-disulfonate, sodium lignosulfonate, sodium dibutylnaphthalenesulfonate or else sodium oleoylmethyltauride, in addition to a diluent or inert material. To prepare the wettable powders, the herbicidal active ingredients are ground finely, for example in customary apparatuses such as hammer mills, blower mills and air-jet mills, and mixed with the formulation auxiliaries, either simultaneously or subsequently.

Emulsifiable concentrates are prepared by dissolving the active ingredient in an organic solvent, for example butanol, cyclohexanone, dimethylformamide, xylene or else higher-boiling aromatics or hydrocarbons or mixtures of the organic solvents with addition of one or more ionic or nonionic surfactants (emulsifiers). Examples of emulsifiers which may be used are: calcium salts of alkylarylsulfonic acids, such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters such as sorbitan fatty acid esters, for example, or polyoxyethylene sorbitan esters such as, for example, polyoxyethylene sorbitan fatty acid esters.

Dusts are obtained by grinding the active ingredient with finely divided solid materials, for example talc, natural clays such as kaolin, bentonite and pyrophyllite, or diatomaceous earth.

Suspension concentrates can be water- or oil-based. They can be prepared, for example, by wet grinding by means of commercially available bead mills and, if appropriate, addition of surfactants as have already been mentioned for example above in the case of the other formulation types.

Emulsions, for example oil-in-water emulsions (EW), can be prepared for example by means of stirrers, colloid mills and/or static mixers using aqueous organic solvents and, if appropriate, surfactants as have already been mentioned for example above in the case of the other formulation types.

Granules can be prepared either by spraying the active ingredient onto adsorptive, granulated inert material or by applying active ingredient concentrates to the surface of carriers such as sand, kaolinites or granulated inert material with the aid of adhesives, for example polyvinylalcohol, sodium polyacrylate or else mineral oils. Suitable active ingredients may also be granulated in the manner conventionally used for the production of fertilizer granules, if desired in a mixture with fertilizers.

As a rule, water-dispersible granules are prepared by conventional processes such as spray drying, fluidized-bed granulation, disk granulation, mixing with high-speed mixers and extrusion without solid inert material.

Regarding the production of disk granules, fluidized-bed granules, extruder granules and spray granules, see, for example, the methods in "Spray-Drying Handbook" 3rd Ed. 1979, G. Goodwin Ltd., London; J. E. Browning, "Agglomeration", Chemical and Engineering 1967, page 147 et seq; "Perry's Chemical Engineer's Handbook", 5th Ed., McGraw-Hill, New York 1973, pp. 8–57.

For further details on the formulation of crop protection products, see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical formulations comprise 0.1 to 99% by weight, in particular 0.1 to 95% by weight, of active ingredient of the formula (I). The active ingredient concentration in wettable powders is, for example, approximately 10 to 95% by weight, the remainder to 100% by weight being composed of customary formulation constituents. In the case of emulsifiable concentrates, the active ingredient concentration may amount to approximately 1 to 90%, preferably 5 to 80% by weight. Formulations in the form of dusts comprise 1 to 30% by weight of active ingredient, preferably in most cases 5 to 20% by weight of active ingredient, sprayable solutions contain approximately 0.05 to 80%, preferably 2 to 50% by weight of active ingredient. In the case of water dispersible granules, the active ingredient content depends partly on whether the active compound is present in liquid or solid form and on which granulation auxiliaries, fillers and the like are being used. The active ingredient content amounts to, for example, between 1 and 95% by weight, preferably to between 10 and 80% by weight in the case of the water-dispersible granules.

In addition, the abovementioned active ingredient formulations may comprise, if appropriate, the conventional adhesives, wetters, dispersants, emulsifiers, penetrants, preservatives, antifreeze agents, solvents, fillers, carriers, colorants, antifoams, evaporation inhibitors, pH regulators or viscosity regulators which are customary in each case.

Based on these formulations, it is also possible to prepare combinations with other pesticidally active substances such as, for example, insecticides, acaricides, herbicides, fungicides, or else with safeners, fertilizers and/or growth regulators, for example in the form of a readymix or a tank mix.

Components in combinations for the active substances according to the invention in formulation mixtures or in the tank mix which can be employed are, for example, known active substances as are described, for example, in Weed Research 26, 441–445 (1986) or "The Pesticide Manual", 11th edition, The British Crop Protection Council and the Royal Soc. of Chemistry, 1997 and the literature cited therein. Examples of known herbicides which can be combined with the compounds of the formula (I) are the following active substances (note: either the common name in accordance with the International Organization for Standardization (ISO) or the chemical name of the compounds, if appropriate together with the customary code number, is given): acetochlor; acifluorfen; aclonifen; AKH 7088, i.e. [[[1-[5-[2-chloro-4-(trifluoromethyl)-phenoxy]-2-nitrophenyl]-2-methoxyethylidene]amino]oxy]acetic acid and its methyl ester; alachlor; alloxydim; ametryn; amidosulfuron; amitrol; AMS, i.e. ammonium sulfamate; anilofos; asulam; atrazine; azimsulfurone (DPX-A8947); aziprotryn; barban; BAS 516 H, i.e. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, i.e. 2-chloro-N,N-di-2-propenylacetamide; CDEC, i.e. 2-chloroallyl diethyl dithiocarbamate; chlomethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, i.e. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, i.e. N-[2-chloro-4-fluoro-5[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; fluropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazapyr; imazamethabenz-methyl; imazaquin and salts such as the ammonium salt; ioxynil; imazethamethapyr; imazethapyr; imazosulfuron; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; metham; methabenzthiazuron; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monolinuron; monuron; monocarbamide dihydrogensulfate; MT 128, i.e. 6-chloro-N-(3-chloro-2-propenyl)-5-methyl-N-phenyl-3-pyridazinamine; MT 5950, i.e. N-[3-chloro-4-(1-methylethyl)phenyl]-2-methylpentanamide; naproanilide; napropamide; naptalam; NC 310, i.e. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham; phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivatives, for example quizalofop-ethyl; quizalofop-P-tefuryl and -ethyl; renriduron; rimsulfuron (DPX-E 9636); S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoro-methyl)phenoxy]-2-naphthalenyl]oxy]propanoic acid and its methyl ester; sulfentrazon (FMC-97285, F-6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-24085); thiobencarb; thifensulfuron-methyl; tiocarbazil; tralkoxydim; tri-allate; triasulfuron; triazofenamide; tribenuron-methyl; triclopyr; tridiphane; trietazine; trifluralin; triflusulfuron and its esters (for example methyl ester, DPX-66037); trimeturon; tsitodef; vernolate; WL 110547, i.e. 5-phenoxy-i-[3-(trifluoromethyl)phenyl]-i H-tetrazole; UBH-509; D-489; LS 82-556; KPP-300; NC-324; NC-330; KH-218; DPX-N8189; SC-0774; DOWCO-535; DK-8910; V-53482; PP-600; MBH-001; KIH-9201; ET-751; KIH-6127 and KIH-2023.

For use, the formulations which are present in commercially available form are, if appropriate, diluted in the customary manner, for example using water in the case of wettable powders, emulsifiable concentrates, dispersions and water-dispersible granules. Preparations in the form of dusts, soil granules, granules for spreading, and sprayable solutions are usually not diluted any further with other inert substances prior to use.

The required application rate of the compounds of the formula (I) varies with the external conditions such as, inter alia, temperature, humidity and the nature of the herbicide used. It can vary within wide limits, for example between 0.001 and 10.0 kg/ha or more of active substance, but it is preferably between 0.005 and 5 kg/ha.

The examples hereinbelow illustrate the invention.

A. CHEMICAL EXAMPLES 1.1 Preparation of 2-[2-chloro-4-methylsulfonyl-3-(3a,4,5, 6a-tetrahydrofuro-[3,2-d]isoxazol-3-yl)benzoyl] cyclohexane-1,3-dione The compound methyl 2-chloro-3-hydroximinoethyl-4-methylsulfonylbenzoate, which is used as starting material, was prepared starting from 2,6-dichlorotoluene in accordance with the method described in DE 19935218.6.

Step 1: Methyl 2-chloromethylsulfonyl-3(3a,4,5,6a-tetrahydrofuro[3,2-d]-isoxazol-3-yl)benzoate 50.0 g (171.4 mmol) of methyl 2-chloro-3-hydroximinomethyl-4-methylsulfonyl-benzoate are dissolved in 600 ml of dimethylformamide, and 24.03 g (180 mmol) of N-chlorosuccinimide are added at room temperature. After the mixture has been stirred for 4 hours it is cooled to 0° C., and 24.03 g (342.8 mmol) of 2,3-dihydrofuran and subsequently 26.02 g (257.1 mmol) of triethylamine are added. After the reaction mixture has been stirred for 16 hours at room temperature, it is concentrated, the residue is taken up in dichloromethane and the mixture is mixed with sodium bicarbonate solution and with water. After evaporation on a rotary evaporator, 63.61 g of crude methyl 2-chloro-4-methylsulfonyl-3-(3a,4,5,6a-tetrahydrofuro[3,2-d]isoxazol-3yl)benzoate are obtained as a viscous dark oil.

Step 2: 2-Chloro-4-methylsulfonyl-3-(3a,4,5,6a-tetrahydrofuro[3,2-d]isoxazol-3-yl)benzoic acid 60.0 g (168.8 mmol) of methyl 2-chloro-4-methylsulfonyl-3-(3a,4,5,6a-tetrahydrofuro[3,2-d]isoxazol-3-yl)benzoate are dissolved in 600 ml of tetrahydrofuran/300 ml of water, and 7.34 g (183.4 mmol) of sodium hydroxide are added. After the reaction mixture has been stirred for 18 hours at room temperature, it is concentrated, brought to pH 2 with 2 N hydrochloric acid and extracted with dichloromethane. This gives 63.6 g of crude 2-chloro-4-methylsulfonyl-3-(3a,4,5,6a-tetrahydrofuro[3,2-d]isoxazol-3yl)benzoic acid as a foam.

Step 3: 3-Oxocyclohex-1-enyl 2-chloro-4-methylsulfonyl-3-(3a,4,5,6a-tetra-hydrofuro[3,2-d]isoxazol-3-yl)benzoate 58.0 g (167.8 mmol) of 2-chloro-4-methylsulfonyl-3-(3a,4,5,6a-tetrahydrofuro[3,2-d]isoxazol-3-yl)-benzoate are dissolved in 600 ml of dichloromethane, and 31.94 g (251.6 mmol) of oxalyl chloride and three drops of dimethylformamide are added at room temperature. After the evolution of gas has ceased (approx. 2 hours), the mixture is refluxed for a further hour. It is subsequently concentrated, and redissolved in 300 ml of dichloromethane. At 0–5° C., a mixture of 19.5 g (173.9 mmol) of 1,3-cyclohexanedione and 17.6 g (173.9 mmol) of triethylamine in 200 ml of dichlormethane is added dropwise. The mixture is stirred for 2 hours and then washed in succession with sodium carbonate solution and sodium chloride solution, and the organic phase is then dried over magnesium sulfate. After removal of the solvent, 64.5 g (87% of theory) of crude 3-oxocyclohex-1-enyl 2-chloro-4-methyl-sulfonyl-3-(3a,4,5,6a-tetrahydrofuro[3,2-d]isoxazol-3-yl)benzoate are obtained.

Step 4: 2-[2-Chloro-4-methylsulfonyl-3-(3a,4,5,6a-tetrahydrofuro[3,2-d]isoxazol-3-yl)benzoyl]cyclohexane-1,3-dione 56.5 g (128.4 mmol) of 3-oxocyclohex-1-enyl 2-chloro-4-methylsulfonyl-3-(3a,4,5,6a-tetrahydrofuro[3,2-d] isoxazol-3-yl)benzoate are dissolved in 700 ml of acetonitrile, 23.39 g (231.2 mmol) of triethylamine and 0.5 ml of acetone cyanohydrin are added, and the mixture is stirred at room temperature. After 16 hours, the mixture is concentrated, dissolved in 200 ml of 2 N sodium hydroxide solution and added dropwise to 300 ml of 2 N hydrochloric acid. The crystals which have precipitated are filtered off with suction and dried in vacuo. This gives 41.35 g (73% of theory) of 2-[2-chloro-4-methylsulfonyl-3-(3a,4,5,6a-tetrahydrofuro[3,2-d]isoxazol-3-yl)-benzoyl]cyclohexane-1,3-dione of melting point 119° C.

1.2. Preparation of 2-[2-chloro-4-ethylsulfonyl-3-(3a,4,5, 6a-tetrahydrofuro[3,2-d]isoxazol-3-yl)-benzoyl] cyclohexane-1,3-dione Step 1: 3-Oxocyclohex-1-enyl 2-chloro-4-ethylsulfonyl-3-(3a,4,5,6a-tetrahydrofuro[3,2-d]isoxazol-3-yl)-benzoate The starting compound used here was prepared starting from 2,6-dichlorotoluene analogously to the method described in DE 19935218.6 using sodium thioethoxide instead of sodium thiomethoxide.

0.9 g (2.5 mmol) of 2-chloro-4-ethylsulfonyl-3-(3a,4,5, 6a-tetrahydrofuro[3,2-d]-isoxazol-3yl)benzoic acid together with 0.31 g (2.8 mmol) of 1,3-cyclohexandione in 50 ml of dichloromethane are treated with 0.53 g (2.8 mmol) of 1-(3-dimethylaminopropyl)-3-ethylcarbodiimi hydrochloride and 0.1 g of N,N-dimethylaminopyridine. After the mixture has been stirred for 16 hours at room temperature, it is washed with 1 N hydrochloric acid and sodium chloride solution and dried over magnesium sulfate. It is filtered with suction and the filtrate is concentrated. This gives 0.66 g (58% of theory) of crude 3-oxocyclohex-1-enyl 2-chloro-4-ethylsulfonyl-3-(3a,4,5,6a-tetrahydrofurro[3,2-d]isoxazol-3-yl)benzoate.

Step 2: 2-[2-Chloro-4-ethylsulfonyl-3-(3a,4,5,6a-tetrahydrofuro[3,2-d]isoxazol-3-yl)benzyl]cyclohexane-1,3-dione 0.65 g (1.4 mmol) of 3-oxocyclohex-1-enyl 2-chloro-4-methylsulfonyl-3-(3a,4,5,6a-tetrahydrofuro[3,2-d]isoxazol-3-yl)benzoate ester is dissolved in 50 ml of acetonitrile, 0.26 g (2.6 mmol) of triethylamine and 1 drop of acetone cyanohydrin are added, and the mixture is stirred at room temperature. After 16 hours, the mixture is concentrated and the residue is dissolved in 10 ml of 2 N sodium hydroxide solution and added dropwise to 20 ml of 2 N hydrochloric acid. The crystals which have precipitated are filtered off with suction and dried in vacuo. This gives 0.41 g (63% of theory) of 2-[2-chloro-4-ethylsulfonyl-3-(3a,4,5,6a-tetrahydrofuro[3,2-d]isoxazol-3-yl)benzoyl]cyclohexane-1, 3-dione of melting point 99° C.

The examples listed in the tables which follow were prepared analogously to abovementioned methods or can be obtained analogously to abovementioned methods.

The following abbreviations were used:

| | | |
|---|---|---|
| Me = methyl | Bu = butyl | Et = ethyl |
| Ph = phenyl | Pr = propyl | Py = pyridyl |
| c = cyclo | i = iso | t = tertiary |
| m.p. = melting point | $R_f$ = retention value | |

TABLE 1

Compounds of the formula (I) according to the invention in which the substituents and symbols have the following meanings:

$R^4 = OH \quad Y = CH_2 \quad Z = CH_2 \quad p = 1$

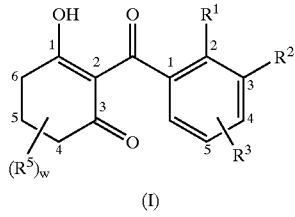

(I)

| No. | $R^1$ | $R^3$ | w | $R^5$ | $R^2$ | Phys. Data |
|---|---|---|---|---|---|---|
| 1 | Cl | 4-SO$_2$Et | 0 | — | (3-methyl-3a,4,5,6-tetrahydro-cyclopenta[d]isoxazole) | $R_f$ = 0.22 (ethyl acetate) m.p. 98–100° C. |
| 2 | Cl | 4-SO$_2$Et | 0 | — | (3-methyl-3a,4,5,6,7,7a-hexahydrobenzo[d]isoxazole) | $R_f$ = 0.29 (ethyl acetate) |
| 3 | Cl | 4-SO$_2$Et | 0 | — | (3-methyl-cycloheptane-fused isoxazoline) | $R_f$ = 0.22 (ethyl acetate) m.p. 98–100° C. |
| 4 | Cl | 4-SO$_2$Et | 0 | — | (3-methyl-pyrano-fused isoxazoline) | $R_f$ = 0.11 (ethyl acetate) |
| 5 | Cl | 4-SO$_2$Et | 0 | — | (3-methyl-furano-fused isoxazoline) | $R_f$ = 0.10 (ethyl acetate) m.p. 120–123° C. |
| 6 | Cl | 4-SO$_2$Et | 0 | — | (3-methyl-cyclohexane with CH$_2$OMe fused isoxazoline) | $R_f$ = 0.19 (ethyl acetate) m.p. 93–96° C. |
| 7 | Cl | 4-SO$_2$Et | 0 | — | (3-methyl-cyclohexane with CH$_2$OMe isomer) | |
| 8 | Cl | 4-SO$_2$Et | 0 | — | (3-methyl-cyclopentanone-fused isoxazoline) | $R_f$ = 0.14 (ethyl acetate) |
| 9 | Cl | 4-SO$_2$Et | 0 | — | (3-methyl-indane-fused isoxazoline) | $R_f$ = 0.24 (ethyl acetate) m.p. 143–147° C. |

TABLE 1-continued

Compounds of the formula (I) according to the invention in which the substituents and symbols have the following meanings:
$R^4 = OH$  $Y = CH_2$  $Z = CH_2$  $p = 1$

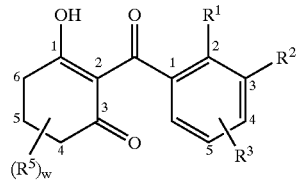

(I)

| No. | $R^1$ | $R^3$ | w | $R^5$ | $R^2$ | Phys. Data |
|---|---|---|---|---|---|---|
| 10 | Cl | 4-SO$_2$Et | 0 | — | (structure) | $R_f$ = 0.29 (ethyl acetate) m.p. 136–138° C. |
| 11 | Cl | 4-SO$_2$Me | 2 | 5-Me | (structure) | $R_f$ = 0.22 (ethyl acetate) |
| 12 | Cl | 4-SO$_2$Et | 0 | — | (structure) | |
| 13 | Cl | 4-SO$_2$Et | 0 | — | (structure) | |
| 14 | Cl | 4-SO$_2$Et | 0 | — | (structure) | |
| 15 | Cl | 4-SO$_2$Et | 0 | — | (structure) | |
| 16 | Cl | 4-SO$_2$Et | 0 | — | (structure) | |
| 17 | Cl | 4-SO$_2$Et | 0 | — | (structure) | |
| 18 | Cl | 4-SO$_2$Et | 0 | — | (structure) | |
| 19 | Cl | 4-SO$_2$Et | 0 | — | (structure) | |

TABLE 1-continued

Compounds of the formula (I) according to the invention in which the substituents and symbols have the following meanings:
R⁴ = OH  Y = CH₂  Z = CH₂  p = 1

(I)

| No. | R¹ | R³ | w | R⁵ | R² | Phys. Data |
|-----|----|----|---|----|----|------------|
| 20 | Cl | 4-SO₂Et | 0 | — | (2-methyl-cyclopenta-fused thiazole) | |
| 21 | Cl | 4-SO₂Et | 0 | — | (2-methyl-tetrahydrobenzothiazole) | |
| 22 | Cl | 4-SO₂Et | 0 | — | (3-methyl-dihydrofuro-isoxazole) | |
| 23 | Cl | 4-SO₂Et | 0 | — | (3-methyl-cyclopenta-isoxazole) | |
| 24 | Cl | 4-SO₂Et | 0 | — | (3-methyl-tetrahydrobenzisoxazole) | |
| 25 | Cl | 4-SO₂Et | 0 | — | (3-methyl-dihydropyrano-isoxazole) | |
| 26 | Cl | 4-SO₂Et | 0 | — | (3-methyl-dihydrofuro-isoxazole) | |
| 27 | Cl | 4-SO₂Me | 0 | — | (3-methyl-hexahydrocyclopenta-isoxazole) | $R_f = 0.21$ (ethyl acetate) |
| 28 | Cl | 4-SO₂Me | 0 | — | (3-methyl-octahydrobenzisoxazole) | $R_f = 0.28$ (ethyl acetate) |

TABLE 1-continued

Compounds of the formula (I) according to the invention in which the substituents and symbols have the following meanings:
R⁴ = OH  Y = CH₂  Z = CH₂  p = 1

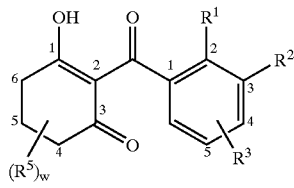

(I)

| No. | R¹ | R³ | w | R⁵ | R² | Phys. Data |
|---|---|---|---|---|---|---|
| 29 | Cl | 4-SO₂Me | 0 | — | (3-methyl-cyclohepta-fused isoxazoline) | $R_f$ = 0.29 (ethyl acetate) |
| 30 | Cl | 4-SO₂Me | 0 | — | (3-methyl-pyrano-fused isoxazoline) | $R_f$ = 0.1 (ethyl acetate) |
| 31 | Cl | 4-SO₂Me | 0 | — | (3-methyl-furo-fused isoxazoline) | $R_f$ = 0.09 (ethyl acetate) |
| 32 | Cl | 4-SO₂Me | 0 | — | (3-methyl-hexahydrobenzisoxazole with CH₂OMe) | |
| 33 | Cl | 4-SO₂Me | 0 | — | (3-methyl-hexahydrobenzisoxazole with CH₂OMe isomer) | |
| 34 | Cl | 4-SO₂Me | 0 | — | (3-methyl-cyclopentanone-fused isoxazoline) | $R_f$ = 0.13 ethyl acetate |
| 35 | Cl | 4-SO₂Me | 0 | — | (3-methyl-indano-fused isoxazoline) | |
| 36 | Cl | 4-SO₂Me | 0 | — | (3-methyl-norbornene-fused isoxazoline) | |

TABLE 1-continued

Compounds of the formula (I) according to the invention in which the substituents and symbols have the following meanings:
R⁴ = OH   Y = CH₂   Z = CH₂   p = 1

| No. | R¹ | R³ | w | R⁵ | R² | Phys. Data |
|-----|----|----|---|----|----|------------|
| 37 | Cl | 4-SO₂Me | 2 | 5-Me | 3-methyl-3a,4,5,6a-tetrahydrofuro[3,2-d]isoxazol-3-yl | |
| 38 | Cl | 4-SO₂Me | 0 | — | 2-methyl-5,6-dihydro-4H-cyclopenta[b]thiophen-2-yl | |
| 39 | Cl | 4-SO₂Me | 0 | — | 2-methyl-4,5,6,7-tetrahydrobenzo[b]thiophen-2-yl | |
| 40 | Cl | 4-SO₂Me | 0 | — | 2-methyl-5,6-dihydro-4H-thieno[2,3-b]thiophen-2-yl | |
| 41 | Cl | 4-SO₂Me | 0 | — | 2-methyl-6,7-dihydrothieno[3,2-b]thiopyran-4(5H)-one | |
| 42 | Cl | 4-SO₂Me | 0 | — | 2-methyl-4,5,6,7-tetrahydrobenzofuran-2-yl | |
| 43 | Cl | 4-SO₂Me | 0 | — | 2-methyl-5,6-dihydro-4H-cyclopenta[b]furan-2-yl | |
| 44 | Cl | 4-SO₂Me | 0 | — | 2-methyl-5,6,7,8-tetrahydroquinolin-2-yl | |
| 45 | Cl | 4-SO₂Me | 0 | — | 2-methyl-6,7-dihydro-5H-cyclopenta[b]pyridin-2-yl | |
| 46 | Cl | 4-SO₂Me | 0 | — | 2-methyl-5,6-dihydro-4H-cyclopenta[d]thiazol-2-yl | |

TABLE 1-continued

Compounds of the formula (I) according to the invention in which the substituents and symbols have the following meanings:
$R^4 = OH$  $Y = CH_2$  $Z = CH_2$  $p = 1$

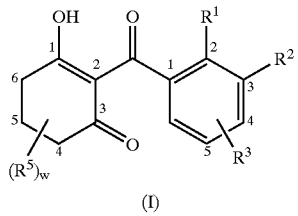

(I)

| No. | $R^1$ | $R^3$ | w | $R^5$ | $R^2$ | Phys. Data |
|---|---|---|---|---|---|---|
| 47 | Cl | 4-SO$_2$Me | 0 | — | (2-methyl-4,5,6,7-tetrahydrobenzothiazol-2-yl) | |
| 48 | Cl | 4-SO$_2$Me | 0 | — | (3-methyl-5,6-dihydro-4H-furo[2,3-d]isoxazol-3-yl) | |
| 49 | Cl | 4-SO$_2$Me | 0 | — | (3-methyl-4,5,6-trihydrocyclopenta[d]isoxazol-3-yl) | |
| 50 | Cl | 4-SO$_2$Me | 0 | — | (3-methyl-4,5,6,7-tetrahydrobenzo[d]isoxazol-3-yl) | |
| 51 | Cl | 4-SO$_2$Me | 0 | — | (3-methyl-4,5-dihydro-6H-pyrano[3,4-d]isoxazol-3-yl) | |
| 52 | Cl | 4-SO$_2$Me | 0 | — | (3-methyl-4H,6H-furo[3,4-d]isoxazol-3-yl) | |
| 53 | Cl | 4-Cl | 0 | — | (3-methyl-3a,4,5,6,6a-hexahydrocyclopenta[d]isoxazol-3-yl) | $R_f = 0.25$ (ethyl acetate) |
| 54 | Cl | 4-Cl | 0 | — | (3-methyl-3a,4,5,6,7,7a-hexahydrobenzo[d]isoxazol-3-yl) | $R_f = 0.30$ (ethyl acetate) |
| 55 | Cl | 4-Cl | 0 | — | (3-methyl-3a,4,5,6,7,8,8a-heptahydrocyclohepta[d]isoxazol-3-yl) | $R_f = 0.32$ (ethyl acetate) |

TABLE 1-continued

Compounds of the formula (I) according to the invention in which the substituents and symbols have the following meanings:
$R^4 = OH \quad Y = CH_2 \quad Z = CH_2 \quad p = 1$

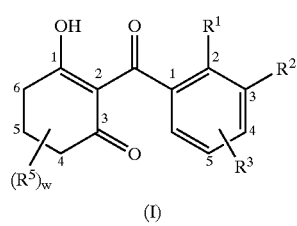

(I)

| No. | $R^1$ | $R^3$ | w | $R^5$ | $R^2$ | Phys. Data |
|---|---|---|---|---|---|---|
| 56 | Cl | 4-Cl | 0 | — | (3-methyl-hexahydropyrano-isoxazole) | $R_f = 0.14$ (ethyl acetate) |
| 57 | Cl | 4-Cl | 0 | — | (3-methyl-tetrahydrofuro-isoxazole) | $R_f = 0.12$ (ethyl acetate) |
| 58 | Cl | 4-Cl | 0 | — | (3-methyl-hexahydrobenzisoxazole with OMe) | |
| 59 | Cl | 4-Cl | 0 | — | (3-methyl-hexahydrobenzisoxazole with OMe) | |
| 60 | Cl | 4-Cl | 0 | — | (3-methyl-cyclopenta-isoxazol-4-one) | $R_f = 0.15$ (ethyl acetate) |
| 61 | Cl | 4-Cl | 0 | — | (3-methyl-indeno-isoxazole) | |
| 62 | Cl | 4-Cl | 0 | — | (3-methyl-methanoindeno-isoxazole) | |
| 63 | Cl | 4-Cl | 0 | — | (3-methyl-furo-isoxazole) | |
| 64 | Cl | 4-Cl | 0 | — | (methyl-cyclopentathiophene) | |

TABLE 1-continued

Compounds of the formula (I) according to the invention in which the substituents and symbols have the following meanings:
$R^4 = OH \quad Y = CH_2 \quad Z = CH_2 \quad p = 1$ (I)

| No. | $R^1$ | $R^3$ | w | $R^5$ | $R^2$ | Phys. Data |
|-----|-------|-------|---|-------|-------|------------|
| 65 | Cl | 4-Cl | 0 | — | 2-methyl-4,5,6,7-tetrahydrobenzo[b]thiophene | |
| 66 | Cl | 4-Cl | 0 | — | 2-methyl-5,6-dihydro-4H-thieno[2,3-b]thiophene | |
| 67 | Cl | 4-Cl | 0 | — | 2-methyl-6,7-dihydrothieno[3,2-b]thiopyran-4(5H)-one | |
| 68 | Cl | 4-Cl | 0 | — | 2-methyl-4,5,6,7-tetrahydrobenzofuran | |
| 69 | Cl | 4-Cl | 0 | — | 2-methyl-5,6-dihydro-4H-cyclopenta[b]furan | |
| 70 | Cl | 4-Cl | 0 | — | 2-methyl-5,6,7,8-tetrahydroquinoline | |
| 71 | Cl | 4-Cl | 0 | — | 2-methyl-6,7-dihydro-5H-cyclopenta[b]pyridine | |
| 72 | Cl | 4-Cl | 0 | — | 2-methyl-5,6-dihydro-4H-cyclopenta[d]thiazole | |
| 73 | Cl | 4-Cl | 0 | — | 2-methyl-4,5,6,7-tetrahydrobenzothiazole | |
| 74 | Cl | 4-Cl | 0 | — | 3-methyl-5,6-dihydro-4H-furo[3,2-d]isoxazole | |

TABLE 1-continued

Compounds of the formula (I) according to the invention in which the substituents and symbols have the following meanings:
$R^4$ = OH   Y = CH$_2$   Z = CH$_2$   p = 1

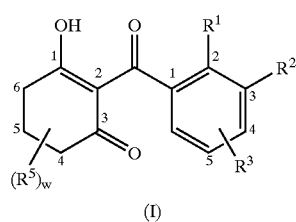

(I)

| No. | $R^1$ | $R^3$ | w | $R^5$ | $R^2$ | Phys. Data |
|---|---|---|---|---|---|---|
| 75 | Cl | 4-Cl | 0 | — | | |
| 76 | Cl | 4-Cl | 0 | — | | |
| 77 | Cl | 4-Cl | 0 | — | | |
| 78 | Cl | 4-Cl | 0 | — | | |
| 79 | Me | 4-SO$_2$Et | 0 | — | | $R_f$ = 0.23 (ethyl acetate) |
| 80 | Me | 4-SO$_2$Et | 0 | — | | $R_f$ = 0.27 (ethyl acetate) |
| 81 | Me | 4-SO$_2$Et | 0 | — | | $R_f$ = 0.30 (ethyl acetate) |
| 82 | Me | 4-SO$_2$Et | 0 | — | | $R_f$ = 0.08 (ethyl acetate) |
| 83 | Me | 4-SO$_2$Et | 0 | — | | $R_f$ = 0.08 (ethyl acetate) |

TABLE 1-continued

Compounds of the formula (I) according to the invention in which the substituents and symbols have the following meanings:
R⁴ = OH  Y = CH₂  Z = CH₂  p = 1

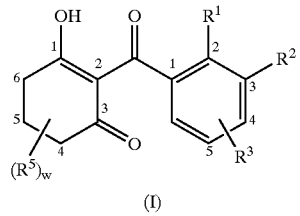

(I)

| No. | R¹ | R³ | w | R⁵ | R² | Phys. Data |
|---|---|---|---|---|---|---|
| 84 | Me | 4-SO₂Et | 0 | — | (3-methyl-hexahydrobenzo[d]isoxazole with CH₂OMe) | |
| 85 | Me | 4-SO₂Et | 0 | — | (3-methyl-hexahydrobenzo[d]isoxazole with CH₂OMe, different position) | |
| 86 | Me | 4-SO₂Et | 0 | — | (3-methyl-cyclopenta[d]isoxazol-4-one) | |
| 87 | Me | 4-SO₂Et | 0 | — | (3-methyl-indeno[d]isoxazole) | |
| 88 | Me | 4-SO₂Me | 0 | — | (3-methyl-methanobridged hexahydroindeno[d]isoxazole) | |
| 89 | Me | 4-SO₂Me | 0 | — | (3-methyl-furo[d]isoxazole) | $R_f = 0.22$ (ethyl acetate) |
| 90 | Me | 4-SO₂Me | 0 | — | (methyl-cyclopenta[b]thiophene) | |
| 91 | Me | 4-SO₂Me | 0 | — | (methyl-tetrahydrobenzo[b]thiophene) | |
| 92 | Me | 4-SO₂Me | 0 | — | (methyl-thieno[3,2-b]thiophene, dihydro) | |

TABLE 1-continued

Compounds of the formula (I) according to the invention in which the substituents and symbols have the following meanings:
R⁴ = OH   Y = CH₂   Z = CH₂   p = 1

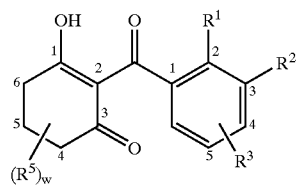

(I)

| No. | R¹ | R³ | w | R⁵ | R² | Phys. Data |
|---|---|---|---|---|---|---|
| 93 | Me | 4-SO₂Me | 0 | — | (2-methyl-4-oxo-5,6-dihydro-4H-thieno[2,3-b]thiopyranyl) | |
| 94 | Me | 4-SO₂Me | 0 | — | (2-methyl-4,5,6,7-tetrahydrobenzofuranyl) | |
| 95 | Me | 4-SO₂Me | 0 | — | (2-methyl-5,6-dihydro-4H-cyclopenta[b]furanyl) | |
| 96 | Me | 4-SO₂Me | 0 | — | (2-methyl-5,6,7,8-tetrahydroquinolinyl) | |
| 97 | Me | 4-SO₂Me | 0 | — | (2-methyl-6,7-dihydro-5H-cyclopenta[b]pyridinyl) | |
| 98 | Me | 4-SO₂Me | 0 | — | (2-methyl-5,6-dihydro-4H-cyclopenta[d]thiazolyl) | |
| 99 | Me | 4-SO₂Me | 0 | — | (2-methyl-4,5,6,7-tetrahydrobenzothiazolyl) | |
| 100 | Me | 4-SO₂Me | 0 | — | (3-methyl-5,6-dihydro-4H-furo[3,2-d]isoxazolyl) | |
| 101 | Me | 4-SO₂Me | 0 | — | (3-methyl-5,6-dihydro-4H-cyclopenta[d]isoxazolyl) | |
| 102 | Me | 4-SO₂Me | 0 | — | (3-methyl-4,5,6,7-tetrahydrobenzo[d]isoxazolyl) | |

TABLE 1-continued

Compounds of the formula (I) according to the invention in which the substituents and symbols have the following meanings:
$R^4 = OH \quad Y = CH_2 \quad Z = CH_2 \quad p = 1$

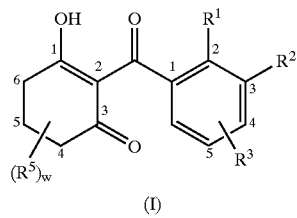

(I)

| No. | $R^1$ | $R^3$ | w | $R^5$ | $R^2$ | Phys. Data |
|-----|-------|-------|---|-------|-------|------------|
| 103 | Me | 4-SO$_2$Me | 0 | — | 3-methyl-4,5,6,7-tetrahydropyrano[3,2-d]isoxazole | |
| 104 | Me | 4-SO$_2$Me | 0 | — | 3-methyl-4,6-dihydrofuro[3,4-d]isoxazole | |
| 105 | Cl | 4-NO$_2$ | 0 | — | 3-methyl-3a,4,5,6-tetrahydro-6aH-cyclopenta[d]isoxazole | |
| 106 | Cl | 4-NO$_2$ | 0 | — | 3-methyl-3a,4,5,6,7,7a-hexahydrobenzo[d]isoxazole | |
| 107 | Cl | 4-NO$_2$ | 0 | — | 3-methyl-3a,4,5,6,7,8-hexahydrocyclohepta[d]isoxazole | |
| 108 | Cl | 4-NO$_2$ | 0 | — | 3-methyl-3a,4,5,6-tetrahydro-7aH-pyrano[3,2-d]isoxazole | |
| 109 | Cl | 4-NO$_2$ | 0 | — | 3-methyl-3a,4,6,6a-tetrahydrofuro[3,4-d]isoxazole | |
| 110 | Cl | 4-NO$_2$ | 0 | — | 3-methyl-6-(methoxymethyl)octahydrobenzo[d]isoxazole | |
| 111 | Cl | 4-NO$_2$ | 0 | — | 3-methyl-5-(methoxymethyl)octahydrobenzo[d]isoxazole | |

TABLE 1-continued

Compounds of the formula (I) according to the invention in which the substituents and symbols have the following meanings:
R⁴ = OH   Y = CH₂   Z = CH₂   p = 1

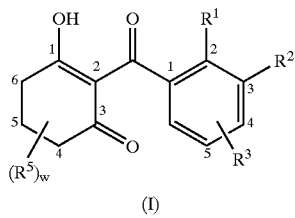

(I)

| No. | R¹ | R³ | w | R⁵ | R² | Phys. Data |
|---|---|---|---|---|---|---|
| 112 | Cl | 4-NO₂ | 0 | — | (3-methyl-4-oxo-3a,5,6,6a-tetrahydrocyclopenta[d]isoxazol-6a-yl) | |
| 113 | Cl | 4-NO₂ | 0 | — | (3-methyl-3a,4-dihydroindeno[1,2-d]isoxazol-8b-yl) | |
| 114 | Cl | 4-NO₂ | 0 | — | (3-methyl-norbornene-fused isoxazoline) | |
| 115 | Cl | 4-NO₂ | 0 | — | (3-methyl-3a,4,5,6a-tetrahydrofuro[3,2-d]isoxazol-6a-yl) | |
| 116 | Cl | 4-NO₂ | 0 | — | (2-methyl-5,6-dihydro-4H-cyclopenta[b]thiophen-2-yl) | |
| 117 | Cl | 4-NO₂ | 0 | — | (2-methyl-4,5,6,7-tetrahydrobenzo[b]thiophen-2-yl) | |
| 118 | Cl | 4-NO₂ | 0 | — | (2-methyl-5,6-dihydrothieno[2,3-b]thiophen-2-yl) | |
| 119 | Cl | 4-NO₂ | 0 | — | (2-methyl-4-oxo-5,6-dihydro-4H-thieno[2,3-b]thiopyran-2-yl) | |
| 120 | Cl | 4-NO₂ | 0 | — | (2-methyl-4,5,6,7-tetrahydrobenzofuran-2-yl) | |

TABLE 1-continued
Compounds of the formula (I) according to the invention in which the substituents and symbols have the following meanings:
$R^4 = OH \quad Y = CH_2 \quad Z = CH_2 \quad p = 1$
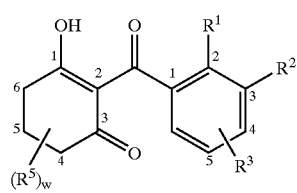
(I)
| No. | $R^1$ | $R^3$ | w | $R^5$ | $R^2$ | Phys. Data |
|---|---|---|---|---|---|---|
| 121 | Cl | 4-NO$_2$ | 0 | — | | |
| 122 | Cl | 4-NO$_2$ | 0 | — | | |
| 123 | Cl | 4-NO$_2$ | 0 | — | | |
| 124 | Cl | 4-NO$_2$ | 0 | — | | |
| 125 | Cl | 4-NO$_2$ | 0 | — | | |
| 126 | Cl | 4-NO$_2$ | 0 | — | | |
| 127 | Cl | 4-NO$_2$ | 0 | — | | |
| 128 | Cl | 4-NO$_2$ | 0 | — | | |
| 129 | Cl | 4-NO$_2$ | 0 | — | | |
| 130 | Cl | 4-NO$_2$ | 0 | — | | |

TABLE 1-continued

Compounds of the formula (I) according to the invention in which the substituents and symbols have the following meanings:
$R^4 = OH \quad Y = CH_2 \quad Z = CH_2 \quad p = 1$

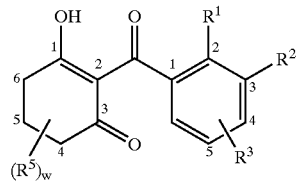

(I)

| No. | R¹ | R³ | w | R⁵ | R² | Phys. Data |
|---|---|---|---|---|---|---|
| 131 | CN | 4-SO₂Et | 0 | — | (3-methyl-3a,4,5,6-tetrahydrocyclopenta[d]isoxazol-3-yl) | |
| 132 | CN | 4-SO₂Et | 0 | — | (3-methyl-3a,4,5,6,7,7a-hexahydrobenzo[d]isoxazol-3-yl) | |
| 133 | CN | 4-SO₂Et | 0 | — | (3-methyl-hexahydrocyclohepta[d]isoxazol-3-yl) | |
| 134 | CN | 4-SO₂Et | 0 | — | (3-methyl-pyrano-fused isoxazoline) | |
| 135 | CN | 4-SO₂Et | 0 | — | (3-methyl-furo-fused isoxazoline) | |
| 136 | CN | 4-SO₂Et | 0 | — | (3-methyl-hexahydrobenzo[d]isoxazol-3-yl with OMe) | |
| 137 | CN | 4-SO₂Et | 0 | — | (3-methyl-hexahydrobenzo[d]isoxazol-3-yl with OMe) | |
| 138 | CN | 4-SO₂Et | 0 | — | (3-methyl-4-oxo-cyclopenta-fused isoxazoline) | |
| 139 | CN | 4-SO₂Et | 0 | — | (3-methyl-indeno-fused isoxazoline) | |

TABLE 1-continued
Compounds of the formula (I) according to the invention in which the substituents and symbols have the following meanings:
$R^4 = OH$  $Y = CH_2$  $Z = CH_2$  $p = 1$
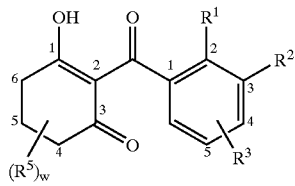
(I)
| No. | R¹ | R³ | w | R⁵ | R² | Phys. Data |
|-----|-----|---------|---|----|----|------------|
| 140 | CN | 4-SO₂Et | 0 | — | | |
| 141 | CN | 4-SO₂Et | 0 | — | | |
| 142 | CN | 4-SO₂Et | 0 | — | | |
| 143 | CN | 4-SO₂Me | 0 | — | | |
| 144 | CN | 4-SO₂Me | 0 | — | | |
| 145 | CN | 4-SO₂Me | 0 | — | | |
| 146 | CN | 4-SO₂Me | 0 | — | | |
| 147 | CN | 4-SO₂Me | 0 | — | | |
| 148 | CN | 4-SO₂Me | 0 | — | | |

TABLE 1-continued

Compounds of the formula (I) according to the invention in which the substituents and symbols have the following meanings:
$R^4$ = OH  Y = CH$_2$  Z = CH$_2$  p = 1

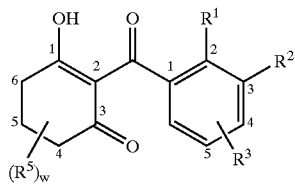

(I)

| No. | R¹ | R³ | w | R⁵ | R² | Phys. Data |
|---|---|---|---|---|---|---|
| 149 | CN | 4-SO₂Me | 0 | — | 2-methyl-cyclopenta[b]furan | |
| 150 | CN | 4-SO₂Me | 0 | — | 2-methyl-5,6,7,8-tetrahydroquinoline | |
| 151 | CN | 4-SO₂Me | 0 | — | 2-methyl-6,7-dihydro-5H-cyclopenta[b]pyridine | |
| 152 | CN | 4-SO₂Me | 0 | — | 2-methyl-cyclopenta[d]thiazole | |
| 153 | CN | 4-SO₂Me | 0 | — | 2-methyl-4,5,6,7-tetrahydrobenzothiazole | |
| 154 | CN | 4-SO₂Me | 0 | — | 3-methyl-furo[3,2-d]isoxazole | |
| 155 | CN | 4-SO₂Me | 0 | — | 3-methyl-cyclopenta[d]isoxazole | |
| 156 | CN | 4-SO₂Me | 0 | — | 3-methyl-4,5,6,7-tetrahydrobenzisoxazole | |
| 157 | CN | 4-SO₂Me | 0 | — | 3-methyl-pyrano[3,4-d]isoxazole | |
| 158 | CN | 4-SO₂Me | 0 | — | 3-methyl-furo[3,4-d]isoxazole | |

TABLE 1-continued
Compounds of the formula (I) according to the invention in which the substituents and symbols have the following meanings:
R⁴ = OH   Y = CH₂   Z = CH₂   p = 1
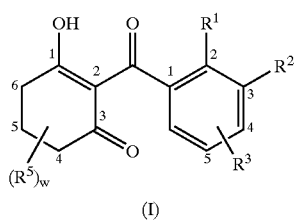
(I)
| No. | R¹ | R³ | w | R⁵ | R² | Phys. Data |
|-----|----|----|---|----|----|------------|
| 159 | Cl | 4-SO₂Me | 1 | 5-Me | | |
| 160 | Cl | 4-SO₂Me | 1 | 5-Me | | |
| 161 | Cl | 4-SO₂Me | 1 | 5-Me | | |
| 162 | Cl | 4-SO₂Me | 1 | 5-Me | | |
| 163 | Cl | 4-SO₂Me | 1 | 5-Me | | |
| 164 | Cl | 4-SO₂Me | 1 | 5-Me | | |
| 165 | Cl | 4-SO₂Me | 1 | 5-Me | | |
| 166 | Cl | 4-SO₂Me | 1 | 5-Me | | |
| 167 | Cl | 4-SO₂Me | 1 | 5-Me | | |

TABLE 1-continued

Compounds of the formula (I) according to the invention in which the substituents and symbols have the following meanings:
$R^4 = OH$  $Y = CH_2$  $Z = CH_2$  $p = 1$ (I)

| No. | $R^1$ | $R^3$ | w | $R^5$ | $R^2$ | Phys. Data |
|---|---|---|---|---|---|---|
| 168 | Cl | 4-SO$_2$Me | 1 | 5-Me | | |
| 169 | Cl | 4-SO$_2$Me | 1 | 5-Me | | |
| 170 | Cl | 4-SO$_2$Me | 1 | 5-Me | | |
| 171 | Cl | 4-SO$_2$Me | 1 | 5-Me | | |
| 172 | Cl | 4-SO$_2$Me | 1 | 5-Me | | |
| 173 | Cl | 4-SO$_2$Me | 1 | 5-Me | | |
| 174 | Cl | 4-SO$_2$Me | 1 | 5-Me | | |
| 175 | Cl | 4-SO$_2$Me | 1 | 5-Me | | |
| 176 | Cl | 4-SO$_2$Me | 1 | 5-Me | | |
| 177 | Cl | 4-SO$_2$Me | 1 | 5-Me | | |

TABLE 1-continued

Compounds of the formula (I) according to the invention in which the substituents and symbols have the following meanings:
R⁴ = OH   Y = CH₂   Z = CH₂   p = 1

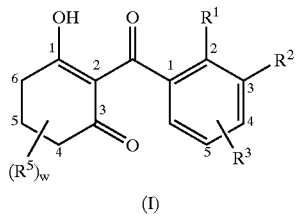

(I)

| No. | R¹ | R³ | w | R⁵ | R² | Phys. Data |
|---|---|---|---|---|---|---|
| 178 | Cl | 4-SO₂Me | 1 | 5-Me | 2-methyl-5,6-dihydro-4H-cyclopenta[d]thiazole | |
| 179 | Cl | 4-SO₂Me | 1 | 5-Me | 2-methyl-4,5,6,7-tetrahydrobenzothiazole | |
| 180 | Cl | 4-SO₂Me | 1 | 5-Me | 3-methyl-5,6-dihydro-4H-furo[3,2-d]isoxazole | |
| 181 | Cl | 4-SO₂Me | 1 | 5-Me | 3-methyl-5,6-dihydro-4H-cyclopenta[d]isoxazole | |
| 182 | Cl | 4-SO₂Me | 1 | 5-Me | 3-methyl-4,5,6,7-tetrahydrobenzo[d]isoxazole | |
| 183 | Cl | 4-SO₂Me | 1 | 5-Me | 3-methyl-4,5-dihydro-6H-pyrano[3,4-d]isoxazole | |
| 184 | Cl | 4-SO₂Me | 1 | 5-Me | 3-methyl-4,6-dihydrofuro[3,4-d]isoxazole | |
| 185 | Cl | 4-SO₂Me | 2 | 5-Me | 3-methyl-3a,4,5,6-tetrahydrocyclopenta[d]isoxazole | |
| 186 | Cl | 4-SO₂Me | 2 | 5-Me | 3-methyl-3a,4,5,6,7,7a-hexahydrobenzo[d]isoxazole | |

TABLE 1-continued
Compounds of the formula (I) according to the invention in which the substituents and symbols have the following meanings:
$R^4 = OH$   $Y = CH_2$   $Z = CH_2$   $p = 1$
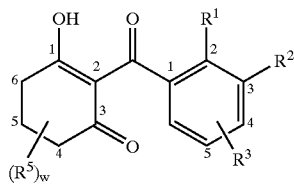
(I)
| No. | $R^1$ | $R^3$ | w | $R^5$ | $R^2$ | Phys. Data |
|---|---|---|---|---|---|---|
| 187 | Cl | 4-SO$_2$Me | 2 | 5-Me | | |
| 188 | Cl | 4-SO$_2$Me | 2 | 5-Me | | |
| 189 | Cl | 4-SO$_2$Me | 2 | 5-Me | | |
| 190 | Cl | 4-SO$_2$Me | 2 | 5-Me | | |
| 191 | Cl | 4-SO$_2$Me | 2 | 5-Me | | |
| 192 | Cl | 4-SO$_2$Me | 2 | 5-Me | | |
| 193 | Cl | 4-SO$_2$Me | 2 | 5-Me | | |
| 194 | Cl | 4-SO$_2$Me | 2 | 5-Me | | |

TABLE 1-continued

Compounds of the formula (I) according to the invention in which the substituents and symbols have the following meanings:
$R^4 = OH$  $Y = CH_2$  $Z = CH_2$  $p = 1$ (I)

| No. | $R^1$ | $R^3$ | w | $R^5$ | $R^2$ | Phys. Data |
|---|---|---|---|---|---|---|
| 195 | Cl | 4-SO$_2$Me | 2 | 5-Me | (structure) | |
| 196 | Cl | 4-SO$_2$Me | 2 | 5-Me | (structure) | |
| 197 | Cl | 4-SO$_2$Me | 2 | 5-Me | (structure) | |
| 198 | Cl | 4-SO$_2$Me | 2 | 5-Me | (structure) | |
| 199 | Cl | 4-SO$_2$Me | 2 | 5-Me | (structure) | |
| 200 | Cl | 4-SO$_2$Me | 2 | 5-Me | (structure) | |
| 201 | Cl | 4-SO$_2$Me | 2 | 5-Me | (structure) | |
| 202 | Cl | 4-SO$_2$Me | 2 | 5-Me | (structure) | |
| 203 | Cl | 4-SO$_2$Me | 2 | 5-Me | (structure) | |
| 204 | Cl | 4-SO$_2$Me | 2 | 5-Me | (structure) | |

TABLE 1-continued

Compounds of the formula (I) according to the invention in which the substituents and symbols have the following meanings:
$R^4 = OH \quad Y = CH_2 \quad Z = CH_2 \quad p = 1$

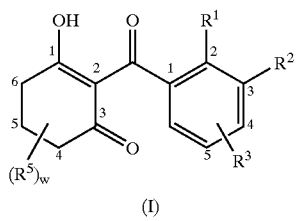

(I)

| No. | $R^1$ | $R^3$ | w | $R^5$ | $R^2$ | Phys. Data |
|---|---|---|---|---|---|---|
| 205 | Cl | 4-SO$_2$Me | 2 | 5-Me | (2-methyl-5,6-dihydro-4H-cyclopenta[d]thiazole) | |
| 206 | Cl | 4-SO$_2$Me | 2 | 5-Me | (2-methyl-4,5,6,7-tetrahydrobenzothiazole) | |
| 207 | Cl | 4-SO$_2$Me | 2 | 5-Me | (3-methyl-4,5-dihydrofuro[3,2-d]isoxazole) | |
| 208 | Cl | 4-SO$_2$Me | 2 | 5-Me | (3-methyl-5,6-dihydro-4H-cyclopenta[d]isoxazole) | |
| 209 | Cl | 4-SO$_2$Me | 2 | 5-Me | (3-methyl-4,5,6,7-tetrahydrobenzo[d]isoxazole) | |
| 210 | Cl | 4-SO$_2$Me | 2 | 5-Me | (3-methyl-4,5,6,7-tetrahydropyrano[3,2-d]isoxazole) | |
| 211 | Cl | 4-SO$_2$Me | 2 | 5-Me | (3-methyl-4,6-dihydrofuro[3,4-d]isoxazole) | |
| 212 | SO$_2$Me | 4-CF$_3$ | 0 | — | (3-methyl-3a,4,5,6-tetrahydrocyclopenta[d]isoxazole) | |
| 213 | SO$_2$Me | 4-CF$_3$ | 0 | — | (3-methyl-3a,4,5,6,7,7a-hexahydrobenzo[d]isoxazole) | |

TABLE 1-continued
Compounds of the formula (I) according to the invention in which the substituents and symbols have the following meanings:
$R^4 = OH$  $Y = CH_2$  $Z = CH_2$  $p = 1$
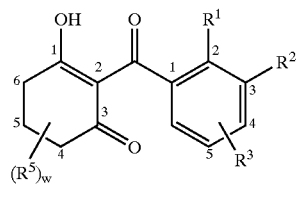
(I)
| No. | $R^1$ | $R^3$ | w | $R^5$ | $R^2$ | Phys. Data |
|-----|-------|-------|---|-------|-------|------------|
| 214 | SO$_2$Me | 4-CF$_3$ | 0 | — | | |
| 215 | SO$_2$Me | 4-CF$_3$ | 0 | — | | |
| 216 | SO$_2$Me | 4-CF$_3$ | 0 | — | | |
| 217 | SO$_2$Me | 4-CF$_3$ | 0 | — | | |
| 218 | SO$_2$Me | 4-CF$_3$ | 0 | — | | |
| 219 | SO$_2$Me | 4-CF$_3$ | 0 | — | | |
| 220 | SO$_2$Me | 4-CF$_3$ | 0 | — | | |
| 221 | SO$_2$Me | 4-CF$_3$ | 0 | — | | |

TABLE 1-continued

Compounds of the formula (I) according to the invention in which the substituents and symbols have the following meanings:
R⁴ = OH  Y = CH₂  Z = CH₂  p = 1

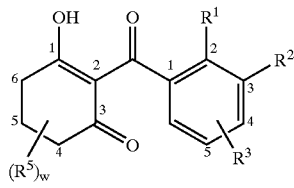

(I)

| No. | R¹ | R³ | w | R⁵ | R² | Phys. Data |
|---|---|---|---|---|---|---|
| 222 | SO₂Me | 4-CF₃ | 0 | — | (3a,6a-dihydrofuro[3,2-d]isoxazol-3-yl with methyl) | |
| 223 | SO₂Me | 4-CF₃ | 0 | — | (2-methyl-5,6-dihydro-4H-cyclopenta[b]thiophene) | |
| 224 | SO₂Me | 4-CF₃ | 0 | — | (2-methyl-4,5,6,7-tetrahydrobenzothiophene) | |
| 225 | SO₂Me | 4-CF₃ | 0 | — | (2-methyl-5,6-dihydro-4H-thieno[3,2-b]thiophene) | |
| 226 | SO₂Me | 4-CF₃ | 0 | — | (2-methyl-5,6-dihydro-thieno[3,2-b]thiopyran-4(4H)-one) | |
| 227 | SO₂Me | 4-CF₃ | 0 | — | (2-methyl-4,5,6,7-tetrahydrobenzofuran) | |
| 228 | SO₂Me | 4-CF₃ | 0 | — | (2-methyl-5,6-dihydro-4H-cyclopenta[b]furan) | |
| 229 | SO₂Me | 4-CF₃ | 0 | — | (2-methyl-5,6,7,8-tetrahydroquinoline) | |
| 230 | SO₂Me | 4-CF₃ | 0 | — | (2-methyl-6,7-dihydro-5H-cyclopenta[b]pyridine) | |
| 231 | SO₂Me | 4-CF₃ | 0 | — | (2-methyl-5,6-dihydro-4H-cyclopenta[d]thiazole) | |

TABLE 1-continued

Compounds of the formula (I) according to the invention in which the substituents and symbols have the following meanings:
$R^4 = OH \quad Y = CH_2 \quad Z = CH_2 \quad p = 1$

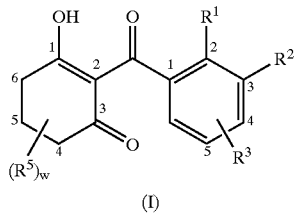

(I)

| No. | $R^1$ | $R^3$ | w | $R^5$ | $R^2$ | Phys. Data |
|-----|-------|-------|---|-------|-------|------------|
| 232 | SO$_2$Me | 4-CF$_3$ | 0 | — | benzothiazole-tetrahydro | |
| 233 | SO$_2$Me | 4-CF$_3$ | 0 | — | methyl-furo-isoxazole dihydro | |
| 234 | SO$_2$Me | 4-CF$_3$ | 0 | — | methyl-cyclopenta-isoxazole dihydro | |
| 235 | SO$_2$Me | 4-CF$_3$ | 0 | — | methyl-tetrahydrobenzisoxazole | |
| 236 | SO$_2$Me | 4-CF$_3$ | 0 | — | methyl-pyrano-isoxazole dihydro | |
| 237 | SO$_2$Me | 4-CF$_3$ | 0 | — | methyl-furo-isoxazole dihydro | |
| 238 | Me | 4-SO$_2$Me | 0 | — | methyl-cyclopenta-isoxazole hexahydro | $R_f = 0.22$ (ethyl acetate) |
| 239 | Me | 4-SO$_2$Me | 0 | — | methyl-benzisoxazole octahydro | $R_f = 0.26$ (ethyl acetate) |
| 240 | Me | 4-SO$_2$Me | 0 | — | methyl-cyclohepta-isoxazole octahydro | $R_f = 0.29$ (ethyl acetate) |

TABLE 1-continued

Compounds of the formula (I) according to the invention in which the substituents and symbols have the following meanings:
R⁴ = OH   Y = CH₂   Z = CH₂   p = 1

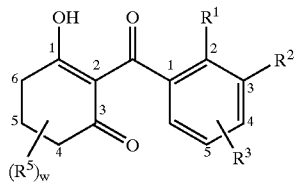

(I)

| No. | R¹ | R³ | w | R⁵ | R² | Phys. Data |
|---|---|---|---|---|---|---|
| 241 | Me | 4-SO₂Me | 0 | — | | $R_f = 0.07$ (ethyl acetate) |
| 242 | Me | 4-SO₂Me | 0 | — | | $R_f = 0.07$ (ethyl acetate) |
| 243 | Me | 4-SMe | 0 | — | | $R_f = 0.3$ (ethyl acetate) |
| 244 | Me | 4-SMe | 0 | — | | $R_f = 0.32$ (ethyl acetate) |
| 245 | Me | 4-SMe | 0 | — | | $R_f = 0.34$ (ethyl acetate) |
| 246 | Me | 4-SMe | 0 | — | | $R_f = 0.36$ (ethyl acetate) |
| 247 | Me | 4-SMe | 0 | — | | $R_f = 0.12$ (ethyl acetate) |
| 248 | Me | 4-SMe | 0 | — | | $R_f = 0.35$ (ethyl acetate) |

TABLE 2

Compounds of the formula (I) according to the invention in which the substituents and symbols have the following meanings:
$R^1$ = Cl  $R^3$ = 4-SO$_2$Et  $R^4$ = OH  Y = CH$_2$
Z = CH$_2$  p = 1

| No. | w | $R^5$ | $R^2$ | Physical data |
|---|---|---|---|---|
| 1 | 2 | 6,6-(Me)$_2$ | | $R_f$ = 0.90 (ethyl acetate) |
| 2 | 2 | 6,6-(Me)$_2$ | | $R_f$ = 0.32 (ethyl acetate) |
| 3 | 2 | 6,6-(Me)$_2$ | | $R_f$ = 0.34 (ethyl acetate) |
| 4 | 2 | 6,6-(Me)$_2$ | | $R_f$ = 0.25 (ethyl acetate) |
| 5 | 2 | 6,6-(Me)$_2$ | | $R_f$ = 0.24 (ethyl acetate) |
| 6 | 2 | 6,6-(Me)$_2$ | | |
| 7 | 2 | 6,6-(Me)$_2$ | | |
| 8 | 2 | 6,6-(Me)$_2$ | | |
| 9 | 2 | 6,6-(Me)$_2$ | | |
| 10 | 2 | 6,6-(Me)$_2$ | | $R_f$ = 0.22 (ethyl acetate) |
| 11 | 2 | 6,6-(Me)$_2$ | | |
| 12 | 2 | 6,6-(Me)$_2$ | | |
| 13 | 2 | 6,6-(Me)$_2$ | | |
| 14 | 2 | 6,6-(Me)$_2$ | | |
| 15 | 2 | 6,6-(Me)$_2$ | | |
| 16 | 2 | 6,6-(Me)$_2$ | | |
| 17 | 2 | 6,6-(Me)$_2$ | | |
| 18 | 2 | 6,6-(Me)$_2$ | | |
| 19 | 2 | 6,6-(Me)$_2$ | | |

TABLE 2-continued

Compounds of the formula (I) according to the invention in which the substituents and symbols have the following meanings:
$R^1$ = Cl   $R^3$ = 4-SO$_2$Et   $R^4$ = OH   Y = CH$_2$
Z = CH$_2$   p = 1

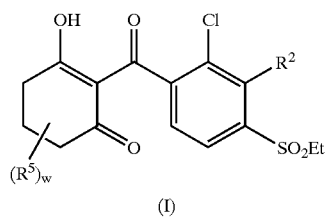

(I)

| No. | w | R$^5$ | R$^2$ | Physical data |
|---|---|---|---|---|
| 20 | 2 | 6,6-(Me)$_2$ |  | |
| 21 | 2 | 6,6-(Me)$_2$ |  | |
| 22 | 2 | 6,6-(Me)$_2$ |  | |
| 23 | 2 | 6,6-(Me)$_2$ |  | |
| 24 | 2 | 6,6-(Me)$_2$ |  | |
| 25 | 2 | 6,6-(Me)$_2$ |  | |
| 26 | 3 | 4-Br-6,6-(Me)$_2$ |  | |
| 27 | 3 | 4-Br-6,6-(Me)$_2$ |  | |
| 28 | 3 | 4-Br-6,6-(Me)$_2$ |  | |

TABLE 2-continued

Compounds of the formula (I) according to the invention in which the substituents and symbols have the following meanings:
$R^1$ = Cl   $R^3$ = 4-SO$_2$Et   $R^4$ = OH   Y = CH$_2$
Z = CH$_2$   p = 1

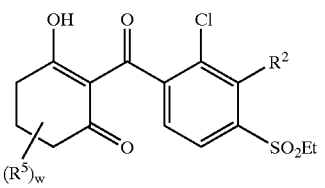

(I)

| No. | w | R$^5$ | R$^2$ | Physical data |
|---|---|---|---|---|
| 29 | 3 | 4-Br-6,6-(Me)$_2$ | 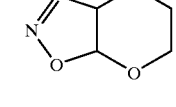 | |
| 30 | 3 | 4-Br-6,6-(Me)$_2$ | 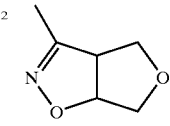 | |
| 31 | 3 | 4-Br-6,6-(Me)$_2$ | 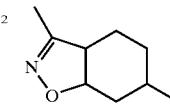 | |
| 32 | 3 | 4-Br-6,6-(Me)$_2$ | 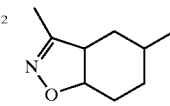 | |
| 33 | 3 | 4-Br-6,6-(Me)$_2$ | 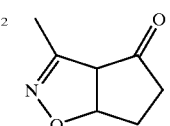 | |
| 34 | 3 | 4-Br-6,6-(Me)$_2$ | 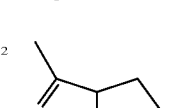 | |
| 35 | 3 | 4-Br-6,6-(Me)$_2$ | 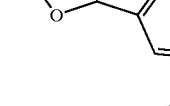 | |
| 36 | 3 | 4-Br-6,6-(Me)$_2$ | 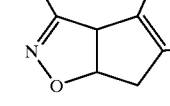 | |

TABLE 2-continued

Compounds of the formula (I) according to the invention in which the substituents and symbols have the following meanings:
$R^1$ = Cl   $R^3$ = 4-SO$_2$Et   $R^4$ = OH   Y = CH$_2$
Z = CH$_2$   p = 1

(I)

| No. | w | R$^5$ | R$^2$ | Physical data |
|---|---|---|---|---|
| 37 | 3 | 4-Br-6,6-(Me)$_2$ | | |
| 38 | 3 | 4-Br-6,6-(Me)$_2$ | | |
| 39 | 3 | 4-Br-6,6-(Me)$_2$ | | |
| 40 | 3 | 4-Br-6,6-(Me)$_2$ | | |
| 41 | 3 | 4-Br-6,6-(Me)$_2$ | | |
| 42 | 3 | 4-Br-6,6-(Me)$_2$ | | |
| 43 | 3 | 4-Br-6,6-(Me)$_2$ | | |
| 44 | 3 | 4-Br-6,6-(Me)$_2$ | | |
| 45 | 3 | 4-Br-6,6-(Me)$_2$ | | |
| 46 | 3 | 4-Br-6,6-(Me)$_2$ | | |
| 47 | 3 | 4-Br-6,6-(Me)$_2$ | | |
| 48 | 3 | 4-Br-6,6-(Me)$_2$ | | |
| 49 | 3 | 4-Br-6,6-(Me)$_2$ | | |
| 50 | 3 | 4-Br-6,6-(Me)$_2$ | | |
| 51 | 3 | 4-Br-6,6-(Me)$_2$ | | |
| 52 | 3 | 4-Br-6,6-(Me)$_2$ | | |
| 53 | 3 | 4-Cl-6,6-(Me)$_2$ | | |
| 54 | 3 | 4-Cl-6,6-(Me)$_2$ | | |
| 55 | 3 | 4-Cl-6,6-(Me)$_2$ | | |

TABLE 2-continued

Compounds of the formula (I) according to the invention in which the substituents and symbols have the following meanings:
R$^1$ = Cl   R$^3$ = 4-SO$_2$Et   R$^4$ = OH   Y = CH$_2$
Z = CH$_2$   p = 1

(I)

| No. | w | R$^5$ | R$^2$ | Physical data |
|---|---|---|---|---|
| 56 | 3 | 4-Cl-6,6-(Me)$_2$ | 3-methyl-hexahydropyrano[3,2-d]isoxazole | |
| 57 | 3 | 4-Cl-6,6-(Me)$_2$ | 3-methyl-hexahydrofuro[3,4-d]isoxazole | |
| 58 | 3 | 4-Cl-6,6-(Me)$_2$ | 3-methyl-hexahydrobenzisoxazole-OMe | |
| 59 | 3 | 4-Cl-6,6-(Me)$_2$ | 3-methyl-hexahydrobenzisoxazole-OMe | |
| 60 | 3 | 4-Cl-6,6-(Me)$_2$ | 3-methyl-cyclopenta-isoxazol-4-one | |
| 61 | 3 | 4-Cl-6,6-(Me)$_2$ | 3-methyl-indeno-isoxazole | |
| 62 | 3 | 4-Cl-6,6-(Me)$_2$ | 3-methyl-furo-isoxazole | |
| 63 | 3 | 4-Cl-6,6-(Me)$_2$ | methyl-cyclopenta-thiophene | |
| 64 | 3 | 4-Cl-6,6-(Me)$_2$ | methyl-tetrahydrobenzothiophene | |
| 65 | 3 | 4-Cl-6,6-(Me)$_2$ | methyl-thieno-thiophene | |
| 66 | 3 | 4-Cl-6,6-(Me)$_2$ | methyl-thieno-thiopyran-4-one | |
| 67 | 3 | 4-Cl-6,6-(Me)$_2$ | methyl-tetrahydrobenzofuran | |
| 68 | 3 | 4-Cl-6,6-(Me)$_2$ | methyl-cyclopenta-furan | |
| 69 | 3 | 4-Cl-6,6-(Me)$_2$ | methyl-tetrahydroquinoline | |
| 70 | 3 | 4-Cl-6,6-(Me)$_2$ | methyl-cyclopenta-pyridine | |
| 71 | 3 | 4-Cl-6,6-(Me)$_2$ | methyl-cyclopenta-thiazole | |
| 72 | 3 | 4-Cl-6,6-(Me)$_2$ | methyl-tetrahydrobenzothiazole | |
| 73 | 3 | 4-Cl-6,6-(Me)$_2$ | 3-methyl-furo-isoxazole | |
| 74 | 3 | 4-Cl-6,6-(Me)$_2$ | 3-methyl-cyclopenta-isoxazole | |

TABLE 2-continued

Compounds of the formula (I) according to the invention in which the substituents and symbols have the following meanings:
$R^1 = Cl$  $R^3 = 4\text{-}SO_2Et$  $R^4 = OH$  $Y = CH_2$
$Z = CH_2$  $p = 1$

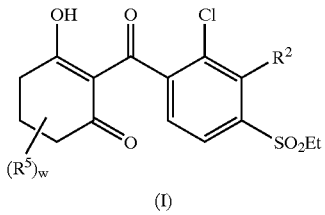

(I)

| No. | w | $R^5$ | $R^2$ | Physical data |
|---|---|---|---|---|
| 75 | 3 | 4-Cl-6,6-(Me)$_2$ | 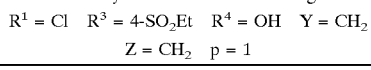 | |
| 76 | 3 | 4-Cl-6,6-(Me)$_2$ | | |
| 77 | 3 | 4-Cl-6,6-(Me)$_2$ | | |

TABLE 3

Compounds of the formula (I) according to the invention in which the substituents and symbols have the following meanings:
$R^3 = 4\text{-}SO_2Et$  $R^4 = OH$  $R^5 = 4\text{-}CH_2\text{-}5, 6\text{-}CH_3$
$Y = CH_2$  $Z = CH_2$  $p = 1$

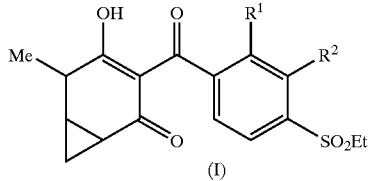

(I)

| No. | $R^1$ | $R^2$ | Physical data |
|---|---|---|---|
| 1 | Cl | | |
| 2 | Cl | | |

TABLE 3-continued

Compounds of the formula (I) according to the invention in which the substituents and symbols have the following meanings:
$R^3 = 4\text{-}SO_2Et$  $R^4 = OH$  $R^5 = 4\text{-}CH_2\text{-}5, 6\text{-}CH_3$
$Y = CH_2$  $Z = CH_2$  $p = 1$

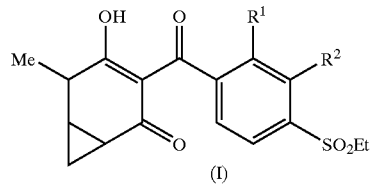

(I)

| No. | $R^1$ | $R^2$ | Physical data |
|---|---|---|---|
| 3 | Cl | | |
| 4 | Cl | | |
| 5 | Cl | | |
| 6 | Cl | | |
| 7 | Cl | | |
| 8 | Cl | | |
| 9 | Cl | | |
| 10 | Cl | | |

TABLE 3-continued

Compounds of the formula (I) according to the invention in which the substituents and symbols have the following meanings:

$R^3$ = 4-SO$_2$Et $\quad$ $R^4$ = OH $\quad$ $R^5$ = 4-CH$_2$-5, 6-CH$_3$
$Y$ = CH$_2$ $\quad$ $Z$ = CH$_2$ $\quad$ $p$ = 1

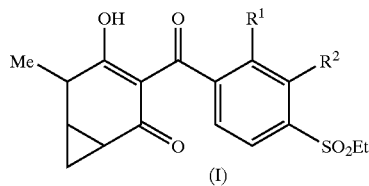

(I)

| No. | R$^1$ | R$^2$ | Physical data |
|---|---|---|---|
| 11 | Cl | | |
| 12 | Cl | | |
| 13 | Cl | | |
| 14 | Cl | | |
| 15 | Cl | | |
| 16 | Cl | | |
| 17 | Cl | | |
| 18 | Cl | | |
| 19 | Cl | | |
| 20 | Cl | | |

TABLE 3-continued

Compounds of the formula (I) according to the invention in which the substituents and symbols have the following meanings:

$R^3$ = 4-SO$_2$Et $\quad$ $R^4$ = OH $\quad$ $R^5$ = 4-CH$_2$-5, 6-CH$_3$
$Y$ = CH$_2$ $\quad$ $Z$ = CH$_2$ $\quad$ $p$ = 1

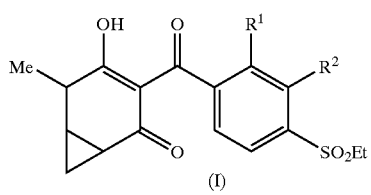

(I)

| No. | R$^1$ | R$^2$ | Physical data |
|---|---|---|---|
| 21 | Cl | | |
| 22 | Cl | | |
| 23 | Cl | | |
| 24 | Cl | | |
| 25 | Cl | | |
| 26 | Me | | |
| 27 | Me | | |
| 28 | Me | | |

TABLE 3-continued

Compounds of the formula (I) according to the invention in which the substituents and symbols have the following meanings:

R³ = 4-SO₂Et    R⁴ = OH     R⁵ = 4-CH₂-5, 6-CH₃
Y = CH₂         Z = CH₂     p = 1

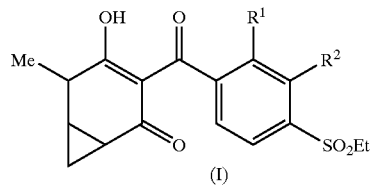

(I)

| No. | R¹ | R² | Physical data |
|---|---|---|---|
| 29 | Me | 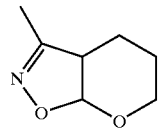 | |
| 30 | Me | 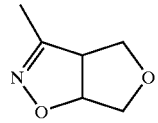 | |
| 31 | Me | 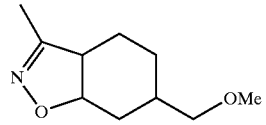 | |
| 32 | Me | 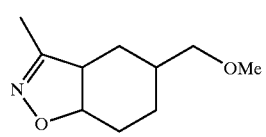 | |
| 33 | Me | 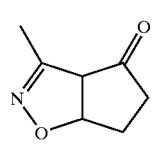 | |
| 34 | Me | 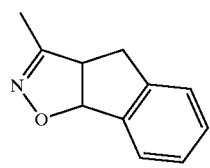 | |
| 35 | Me | 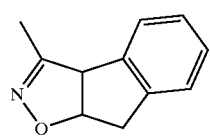 | |
| 36 | Me | 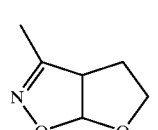 | |
| 37 | Me | 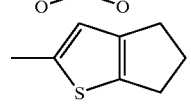 | |

TABLE 3-continued

Compounds of the formula (I) according to the invention in which the substituents and symbols have the following meanings:

R³ = 4-SO₂Et    R⁴ = OH     R⁵ = 4-CH₂-5, 6-CH₃
Y = CH₂         Z = CH₂     p = 1

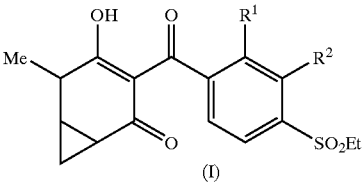

(I)

| No. | R¹ | R² | Physical data |
|---|---|---|---|
| 38 | Me | 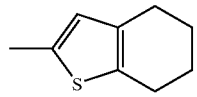 | |
| 39 | Me | 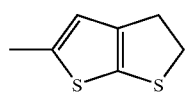 | |
| 40 | Me | 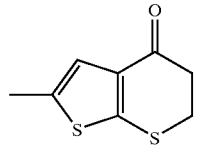 | |
| 41 | Me | 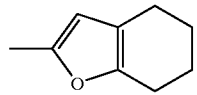 | |
| 42 | Me | 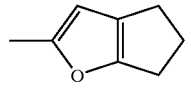 | |
| 43 | Me | 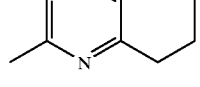 | |
| 44 | Me | 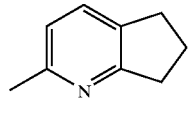 | |
| 45 | Me | 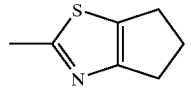 | |
| 46 | Me | 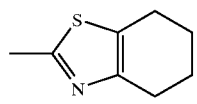 | |

TABLE 3-continued

Compounds of the formula (I) according to the invention in which the substituents and symbols have the following meanings:

R³ = 4-SO₂Et    R⁴ = OH    R⁵ = 4-CH₂-5, 6-CH₃
Y = CH₂    Z = CH₂    p = 1

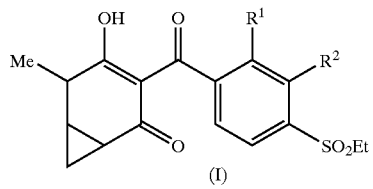

(I)

| No. | R¹ | R² | Physical data |
|---|---|---|---|
| 47 | Me | (3-methyl-fused isoxazole-furan bicycle) | |
| 48 | Me | (3-methyl-cyclopenta-isoxazole) | |
| 49 | Me | (3-methyl-tetrahydrobenzisoxazole) | |
| 50 | Me | (3-methyl-dihydropyrano-isoxazole) | |
| 51 | Me | (3-methyl-dihydrofuro-isoxazole) | |

TABLE 4

Compounds of the formula (I) according to the invention in which the substituents and symbols have the following meanings:

R¹ = Cl    R³ = 5-SO₂Et    R⁴ = OH    Y = CH₂
Z = CH₂    p = 1

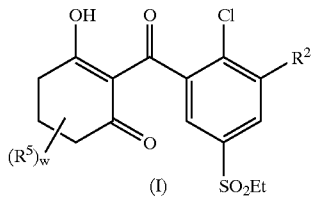

(I)

| No. | w | R⁵ | R² | Physical data |
|---|---|---|---|---|
| 1 | 0 | — | (3-methyl hexahydrocyclopenta-isoxazole) | |
| 2 | 0 | — | (3-methyl octahydrobenzisoxazole) | |
| 3 | 0 | — | (3-methyl cycloheptane-fused isoxazole) | |
| 4 | 0 | — | (3-methyl pyrano-isoxazole) | |
| 5 | 0 | — | (3-methyl furo-isoxazole) | |
| 6 | 0 | — | (3-methyl octahydrobenzisoxazole-CH₂OMe) | |
| 7 | 0 | — | (3-methyl octahydrobenzisoxazole with CH₂OMe) | |
| 8 | 0 | — | (3-methyl cyclopenta-isoxazolone) | |

TABLE 4-continued

Compounds of the formula (I) according to the invention in which the substituents and symbols have the following meanings:

R¹ = Cl    R³ = 5-SO₂Et    R⁴ = OH    Y = CH₂
Z = CH₂    p = 1

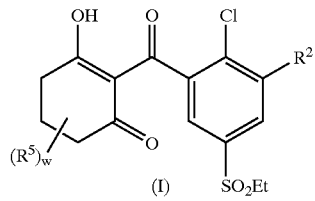

| No. | w | R⁵ | R² | Physical data |
|---|---|---|---|---|
| 9 | 0 | — | 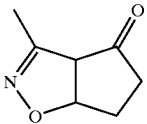 | |
| 10 | 0 | — | 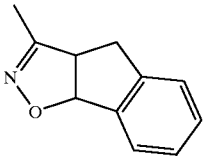 | |
| 11 | 0 | — | 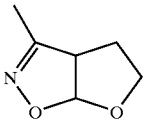 | |
| 12 | 0 | — | 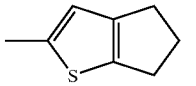 | |
| 13 | 0 | — | 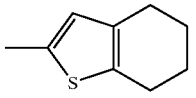 | |
| 14 | 0 | — | 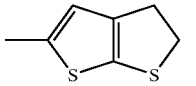 | |
| 15 | 0 | — | 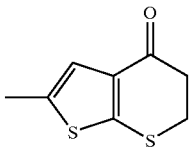 | |
| 16 | 0 | — | 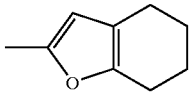 | |
| 17 | 0 | — | 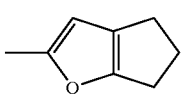 | |

TABLE 4-continued

Compounds of the formula (I) according to the invention in which the substituents and symbols have the following meanings:

R¹ = Cl    R³ = 5-SO₂Et    R⁴ = OH    Y = CH₂
Z = CH₂    p = 1

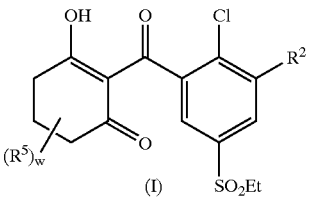

| No. | w | R⁵ | R² | Physical data |
|---|---|---|---|---|
| 18 | 0 | — | 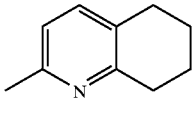 | |
| 19 | 0 | — | 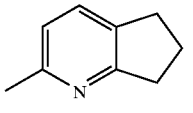 | |
| 20 | 0 | — | 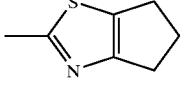 | |
| 21 | 0 | — | 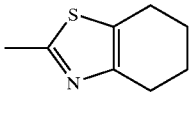 | |
| 22 | 0 | — | 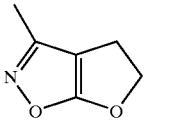 | |
| 23 | 0 | — | 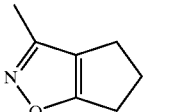 | |
| 24 | 0 | — | 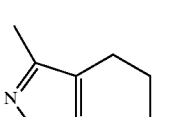 | |
| 25 | 0 | — | 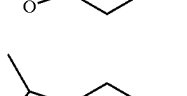 | |
| 26 | 0 | — | 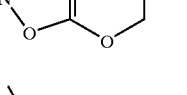 | |

TABLE 4-continued

Compounds of the formula (I) according to the invention in which the substituents and symbols have the following meanings:

R¹ = Cl   R³ = 5-SO$_2$Et   R⁴ = OH   Y = CH$_2$
Z = CH$_2$   p = 1

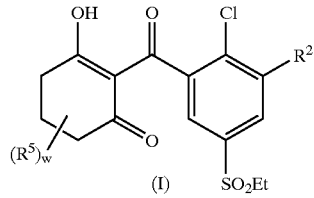

(I)

| No. | w | R⁵ | R² | Physical data |
|---|---|---|---|---|
| 27 | 1 | 5-Me | 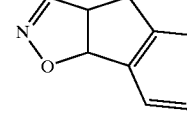 | |
| 28 | 1 | 5-Me | 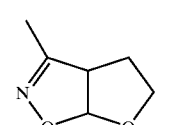 | |
| 29 | 1 | 5-Me | 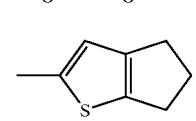 | |
| 30 | 1 | 5-Me | 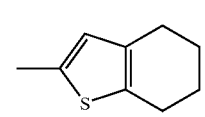 | |
| 31 | 1 | 5-Me | 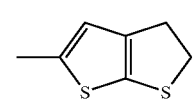 | |
| 32 | 1 | 5-Me | 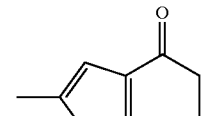 | |
| 33 | 1 | 5-Me | 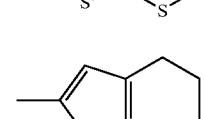 | |
| 34 | 1 | 5-Me | 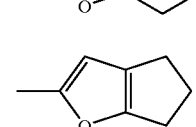 | |

TABLE 4-continued

Compounds of the formula (I) according to the invention in which the substituents and symbols have the following meanings:

R¹ = Cl   R³ = 5-SO$_2$Et   R⁴ = OH   Y = CH$_2$
Z = CH$_2$   p = 1

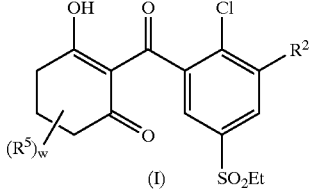

(I)

| No. | w | R⁵ | R² | Physical data |
|---|---|---|---|---|
| 35 | 1 | 5-Me | 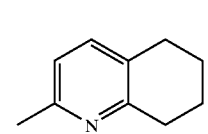 | |
| 36 | 1 | 5-Me | | |
| 37 | 1 | 5-Me | | |
| 38 | 1 | 5-Me | | |
| 39 | 1 | 5-Me | | |
| 40 | 1 | 5-Me | | |
| 41 | 1 | 5-Me | | |
| 42 | 1 | 5-Me | | |
| 43 | 1 | 5-Me | | |

TABLE 4-continued

Compounds of the formula (I) according to the invention in which the substituents and symbols have the following meanings:

R¹ = Cl   R³ = 5-SO₂Et   R⁴ = OH   Y = CH₂
Z = CH₂   p = 1

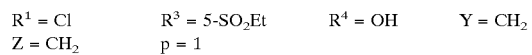

| No. | w | R⁵ | R² | Physical data |
|-----|---|-----|-----|---------------|
| 44 | 1 | 5-Me | 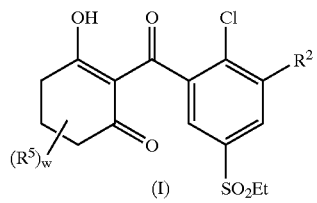 | |
| 45 | 1 | 5-Me | | |
| 46 | 1 | 5-Me | | |
| 47 | 1 | 5-Me | | |
| 48 | 1 | 5-Me | | |
| 49 | 1 | 5-Me | | |
| 50 | 1 | 5-Me | | |
| 51 | 1 | 5-Me | | |
| 52 | 2 | 5,5-(Me)₂ | | |

TABLE 4-continued

Compounds of the formula (I) according to the invention in which the substituents and symbols have the following meanings:

R¹ = Cl   R³ = 5-SO₂Et   R⁴ = OH   Y = CH₂
Z = CH₂   p = 1

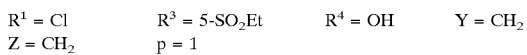

| No. | w | R⁵ | R² | Physical data |
|-----|---|-----|-----|---------------|
| 53 | 2 | 5,5-(Me)₂ | 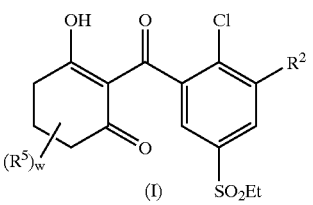 | |
| 54 | 2 | 5,5-(Me)₂ | | |
| 55 | 2 | 5,5-(Me)₂ | | |
| 56 | 2 | 5,5-(Me)₂ | | |
| 57 | 2 | 5,5-(Me)₂ | | |
| 58 | 2 | 5,5-(Me)₂ | | |
| 59 | 2 | 5,5-(Me)₂ | | |
| 60 | 2 | 5,5-(Me)₂ | | |

TABLE 4-continued

Compounds of the formula (I) according to the invention in which the substituents and symbols have the following meanings:

R¹ = Cl  R³ = 5-SO₂Et  R⁴ = OH  Y = CH₂
Z = CH₂  p = 1

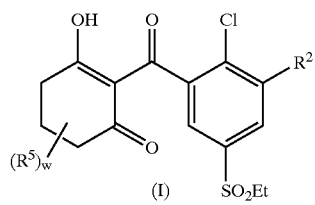

| No. | w | R⁵ | R² | Physical data |
|-----|---|------|-----|------|
| 61 | 2 | 5,5-(Me)₂ | | |
| 62 | 2 | 5,5-(Me)₂ | | |
| 63 | 2 | 5,5-(Me)₂ | | |
| 64 | 2 | 5,5-(Me)₂ | | |
| 65 | 2 | 5,5-(Me)₂ | | |
| 66 | 2 | 5,5-(Me)₂ | | |
| 67 | 2 | 5,5-(Me)₂ | | |
| 68 | 2 | 5,5-(Me)₂ | | |

TABLE 4-continued

Compounds of the formula (I) according to the invention in which the substituents and symbols have the following meanings:

R¹ = Cl  R³ = 5-SO₂Et  R⁴ = OH  Y = CH₂
Z = CH₂  p = 1

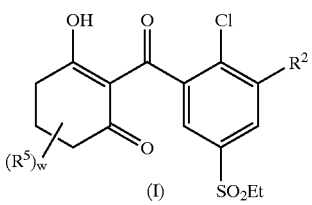

| No. | w | R⁵ | R² | Physical data |
|-----|---|------|-----|------|
| 69 | 2 | 5,5-(Me)₂ | | |
| 70 | 2 | 5,5-(Me)₂ | | |
| 71 | 2 | 5,5-(Me)₂ | | |
| 72 | 2 | 5,5-(Me)₂ | | |
| 73 | 2 | 5,5-(Me)₂ | | |
| 74 | 2 | 5,5-(Me)₂ | | |
| 75 | 2 | 5,5-(Me)₂ | | |
| 76 | 2 | 5,5-(Me)₂ | | |

B. FORMULATION EXAMPLES

1. Dust
A dust is obtained by mixing 10 parts by weight of a compound of the formula (I) and 90 parts by weight of talc as inert substance and comminuting the mixture in a hammer mill.

2. Dispersible Powder
A wettable powder which is readily dispersible in water is obtained by mixing 25 parts by weight of a compound of the formula (I), 64 parts by weight of kaolin-containing quartz as inert material, 10 parts by weight of potassium lignosulfonate and 1 part by weight of sodium oleoylmethyltauride as wetter and dispersant and grinding the mixture in a pinned-disk mill.

3. Dispersion Concentrate
A dispersion concentrate which is readily dispersible in water is obtained by mixing 20 parts by weight of a compound of the formula (I), 6 parts by weight of alkylphenol polyglycol ether (®Triton X 207), 3 parts by weight of isotridecanolpolyglycol ether (8 EO) and 71 parts by weight of paraffinic mineral oil (boiling range, for example, approx. 255 to above 277° C.) and grinding the mixture in a friction ball mill to a fineness of under 5 microns.

4. Emulsifiable Concentrate
An emulsifiable concentrate is obtained from 15 parts by weight of a compound of the formula (I), 75 parts by weight of cyclohexanone as solvent and 10 parts by weight of ethoxylated nonylphenol as emulsifier.

5. Water-dispersible Granules
Water-dispersible granules are obtained by mixing 75 parts by weight of a compound of the formula (I), 10 parts by weight of calcium lignosulfonate, 5 parts by weight of sodium lauryl sulfate, 3 parts by weight of polyvinyl alcohol and 7 parts by weight of kaolin, grinding the mixture in a pinned-disk mill and granulating the powder in a fluidized bed by spraying on water as granulating fluid.

Water-dispersible granules are also obtained by homogenizing and precomminuting 25 parts by weight of a compound of the formula (I), 5 parts by weight of sodium 2,2'-dinaphthylmethane-6,6'-disulfonate, 2 parts by weight of sodium oleoylmethyltauride, 1 parts by weight of polyvinyl alcohol, 17 parts by weight of calcium carbonate and 50 parts by weight of water in a colloid mill, subsequently grinding the mixture in a bead mill and atomizing and drying the suspension thus obtained in a spray tower by means of a single-substance nozzle.

C. BIOLOGICAL EXAMPLES

1. Pre-emergence Herbicidal Action
Seeds of monocotyledonous and dicotyledonous harmful plants are placed in sandy loam in cardboard pots and covered with soil. The compounds according to the invention which are formulated in the form of wettable powders or emulsion concentrates, are then applied to the surface of the covering soil at a rate of 1 kg or less of active substance per hectare (converted) as aqueous suspension or emulsion at an application rate of 600 to 800 l of water per ha (converted). After the treatment, the pots are placed in the greenhouse and kept under good growth conditions for the weeds. Visual scoring of the plant damage or the adverse effect on emergence was done after the test plants had emerged after an experimental period of 3 to 4 weeks in comparison with untreated controls. A large number of compounds according to the invention have an outstanding herbicidal action against the harmful plants.

2. Post-emergence Herbicidal Action
Seeds of monocotyledonous and dicotyledonous weeds are placed in sandy loam soil in cardboard pots, covered with soil and grown in the greenhouse under good growth conditions. Two to three weeks after sowing, the experimental plants are treated at the three-leaf stage. The compounds according to the invention, which are formulated as wettable powders or as emulsion concentrates, are sprayed at a rate of 1 kg of active substance or less per hectare (converted) onto the green plant organs at an application rate of 600 to 800 l of water per ha (converted). After the experimental plants have remained in the greenhouse for approx. 3 to 4 weeks under optimal growth conditions, the effect of the compositions is scored visually in comparison with untreated controls. The compounds according to the invention also have a good herbicidal action against a broad spectrum of economically important monocotyledonous and dicotyledonous harmful plants when applied post-emergence. A large number of compositions according to the invention have an outstanding herbicidal action against the harmful plants.

3. Action on Harmful Plants in Rice
Typical harmful plants in rice crops are grown in the greenhouse under paddy rice conditions (depth of the water: 2–3 cm). After the treatment with the formulated compounds according to the invention at a rate of 1 kg of active substance or less per hectare (converted), the test plants are placed in the greenhouse under optimal growth conditions and kept in this way during the entire test period. About three weeks after application, evaluation is carried out by means of visually scoring the test plants in comparison with untreated controls. The compounds according to the invention have a very good herbicidal action against harmful plants. A large number of compounds according to the invention show an outstanding herbicidal action against the harmful plants.

4. Crop Plant Tolerance
In further greenhouse tests, seeds of a relatively large number of crop plants and monocotyledonous and dicotyledonous harmful plants are placed in sandy loam soil and covered with soil. Some of the pots are immediately treated as described under item 1, while the remaining plants are placed in the greenhouse until the plants have developed two to three true leaves and then sprayed with the compound of the formula (I) according to the invention at various rates. Four to five weeks after the application and standing time in the greenhouse, it is found by means of visually scoring that the compounds according to the invention generally leave dicotyledonous crops such as, for example, soybean and sugarbeet undamaged or almost undamaged, pre and post-emergence, even at high doses of active substance. In addition, some substances also leave graminaceous crops, such as, for example, barley, wheat and rice, unharmed. The compounds of the formula (I) show a high selectivity in most cases and are therefore suitable for controlling undesired vegetation in agricultural crops.

5. Comparative Experiments
Analogously to the experimental conditions mentioned under item 2 (post-emergence herbicidal action), compound No. 1.1 according to the invention was compared with a prior-art compound with regard to its effect against Setaria species. The experimental results show that the compound according to the invention has a more potent action against Setaria species than the prior-art compound, even at a lower application rate.

| Comparison compounds | Rate [g ai/ha] | Action in [%] against SETFA | SETVI |
|---|---|---|---|
| 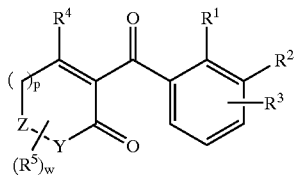<br>Compound No. 1.1 according to the invention | 150<br>75<br>38 | 95<br>90<br>85 | 90<br>70<br>70 |
| 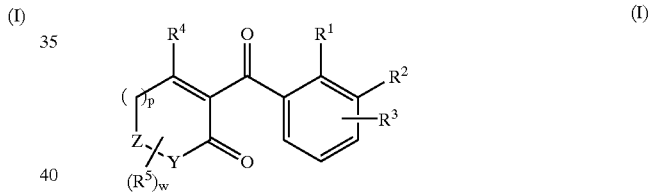<br>Compound disclosed in WO 96/26200 | 200<br>100<br>50 | 50<br>20<br>10 | 40<br>20<br>10 |

The abbreviations in the table denote:
SETFA *Setaria faberii*
SETVI *Setaria viridis*
ai active ingredient

What is claimed is:

1. A heterocyclyl-substituted benzoylcyclohexanedione of the formula (I) or its salt

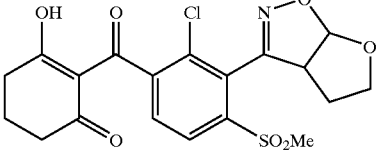

in which
- $R^1$ and $R^3$ independently from each other are chlorine, bromine, methyl, methlysulfonyl, ethylsulfonyl, trifluoromethyl, cyano, or nitro;
- $R^2$ is 4,5-dihydroisoxazol-3-yl, which is substituted by radicals selected from the group consisting of $R^6$, halogen, cyano, nitro, hydroxy, oxo, ($C_1$–$C_4$)-alkyl, halogen-($C_1$–$C_4$)-alkyl, ($C_1$–$C_4$)-alkoxy, halogen-($C_1$–$C_4$)-alkoxy, and di-($C_1$–$C_4$)-alkylamino, and which is condensed in 4,5-position with a 3- to 8-membered, saturated, partially saturated, unsaturated, or aromatic carbocycle wherein one of the carbon atoms in the carbocycle is replaced by a heteroatom selected from the group consisting of oxygen, nitrogen, and sulfur;
- $R^4$ is hydroxy;
- $R^5$ is methyl;
- $R^6$ is cyanomethyl, methoxymethyl, ethoxymethyl, methylsulfenylmethyl, methylsulfinylmethyl, methylsulfonylmethyl, ethylsulfenylmethyl, ethylsulfinylmethyl, or ethylsulfonylmethyl;
- p is 1;
- v is 0, 1, or 2;
- w is 0, 1, or 2; and
- Y and Z are $CH_2$.

2. A heterocyclyl-substituted benzoylcyclohexanedione of the formula (I) or its salt

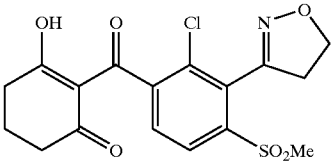

in which
- $R^1$ and $R^3$ independently from each other are chlorine, bromine, methyl, methlysulfonyl, ethylsulfonyl, trifluoromethyl, cyano, or nitro;
- $R^2$ is 4,5-dihydroisoxazol-3-yl, is substituted selected from the group consisting of $R^6$, halogen, cyano, nitro, hydroxy, oxo, ($C_1$–$C_4$)-alkyl, halogen-($C_1$–$C_4$)-alkyl, ($C_1$–$C_4$)-alkoxy, halogen-($C_1$–$C_4$)-alkoxy, and di-($C_1$–$C_4$)-alkylamino, and which is condensed in 4,5-position with a 3- to 8-membered, saturated, partially saturated, unsaturated, or aromatic ring having 1 to 4 hetero atoms selected from the group consisting of oxygen, nitrogen, and sulfur;
- $R^4$ is hydroxy;
- $R^5$ is methyl;
- $R^6$ is cyanomethyl, methoxymethyl, ethoxymethyl, methylsulfenylmethyl, methylsulfinylmethyl, methylsulfonylmethyl, ethylsulfenylmethyl, ethylsulfinylmethyl, or ethylsulfonylmethyl;
- p is 1;
- v is 0, 1, or 2;
- w is 0, 1, or 2; and
- Y and Z are $CH_2$.

3. A benzoylcyclohexanedione as claimed in claim 2, wherein $R^2$ is a radical selected from the group consisting of

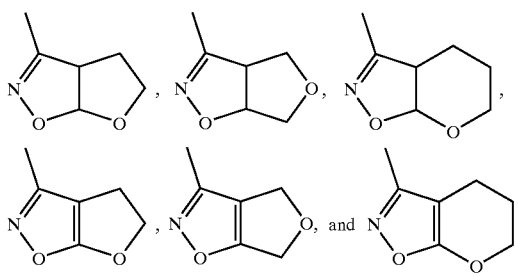

4. A herbicidal composition, which has a herbicidally active content of one or more compounds of the formula (I) according to claim 2 and an inert carrier.

5. A herbicidal composition as claimed in claim 4 further comprising one or more formulation auxiliaries.

6. A compound of the formula (III)

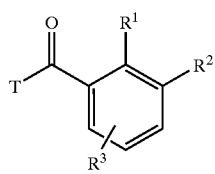

in which T is $(C_1-C_4)$-alkoxy, hydroxyl or halogen, and $R^1$, $R^2$ and $R^3$ have the meanings given in claim 2.

7. A method for controlling undesired plants, which comprises applying an effective amount of one or more compounds of the formula (I) according to claim 2 to the undesired plants or to the location comprising the undesired plants.

8. The method as claimed in claim 7, wherein the location comprising the undesired plants further comprises crops of useful plants.

9. The method as claimed in claim 8, wherein the undesired plants are Setaria species and the crops are maize.

10. The method as claimed in claim 8, wherein the useful plants are transgenic plants.

11. A method for controlling undesired plants, which comprises applying an effective amount of the herbicidal composition according to claim 4, to the undesired plants or to the location comprising the undesired plants.

12. A benzoylcyclohexanedione

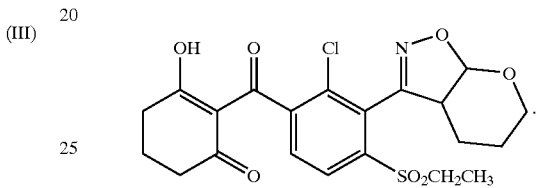

* * * * *